United States Patent
Farmer et al.

(10) Patent No.: US 8,618,152 B2
(45) Date of Patent: Dec. 31, 2013

(54) INHIBITORS OF SERINE PROTEASES, PARTICULARLY HCV NS3-NS4A PROTEASES

(75) Inventors: Luc J. Farmer, Foxboro, MA (US); Robert B. Perni, Marlborough, MA (US); Govinda Rao Bhisetti, Lexington, MA (US); Keith P. Wilson, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/238,386

(22) Filed: Sep. 21, 2011

(65) Prior Publication Data
US 2012/0014914 A1  Jan. 19, 2012

Related U.S. Application Data

(63) Continuation of application No. 12/169,209, filed on Jul. 8, 2008, now abandoned, which is a continuation of application No. 10/821,793, filed on Apr. 9, 2004, now abandoned.

(60) Provisional application No. 60/513,765, filed on Oct. 23, 2003.

(51) Int. Cl.
*A61K 31/4178* (2006.01)
*A61K 31/4025* (2006.01)
*C07D 403/12* (2006.01)
*C07D 207/09* (2006.01)

(52) U.S. Cl.
USPC ......... 514/397; 514/422; 548/314.7; 548/518

(58) Field of Classification Search
USPC .................... 514/397, 422; 548/314.7, 518
See application file for complete search history.

(56) References Cited

U.S. PATENT DOCUMENTS

| | | | |
|---|---|---|---|
| 4,499,082 A | 2/1985 | Shenvi et al. | |
| 5,384,410 A | 1/1995 | Kettner | |
| 5,866,684 A | 2/1999 | Attwood et al. | |
| 6,774,212 B2 | 8/2004 | Han | |

FOREIGN PATENT DOCUMENTS

| | | |
|---|---|---|
| EP | 0417721 | 9/1990 |
| WO | 9212140 | 7/1992 |
| WO | 9817679 | 4/1998 |
| WO | 0102424 | 1/2001 |
| WO | 0140262 | 6/2001 |
| WO | 0174768 | 10/2001 |
| WO | 0208244 | 1/2002 |
| WO | 0208251 | 1/2002 |
| WO | 0208256 | 1/2002 |
| WO | 0218369 | 3/2002 |
| WO | WO 02/18369 | * 3/2002 |
| WO | 03087092 | 10/2003 |

OTHER PUBLICATIONS

Patani et al. "Bioisosterism: A Rational Approach in Drug Design" Chem. Rev., 1996, vol. 96, pp. 3147-3176.*
Han et al., "α-Ketoamides, α-Ketoesters and α-Diketones as HCV NS3 Protease Inhibitors", Bioorganic & Medicinal Chemistry Letters, vol. 10, pp. 711-713, 2000.
Burkhart et al., "Preparation of a α-Keto Ester Enol Acetates as Potential Prodrugs of Human Neutrophil Elastase Inhibitors", Bioorganic and Medicinal Chemistry Letters, vol. 8, No. 1-6, pp. 765-770.
Fumihiko Akohoshi, "Chymas Inhibitors and Their Therapeutic Potential", Drugs of the Future, vol. 27, No. 8, pp. 765-770, 2002.
Bastos et al., "Inhibitors of Human Heart Chymase Based on a Peptide Library", Proc. Natl. Acad. Sci. USA, vol. 92, No. 15, pp. 6738-6742, 1995.
Llinas-Brunet et al., "Studies on the C-Terminal of Hexapeptide Inhibitors of the Hepatitis C Virus Serine Protease", Bioorganic & Medicinal Chemistry Letters, vol. 8, No. 19, 1998.
Perni et al., "Inhibitors of Hepatitis C Virus, NS3, 4A Protease 2 Warhead SAR and Optimization", Bioorganic & Medicinal Chemistry Letters, vol. 14, No. 6, 2004.
Sasaki et al. "A Novel Stereodivergent Synthesis of Optically Pure cis- and trans-3-Substituted Proline Derivatives" J. Org. Chem. 1997, 765-770.
Patani et al. "Bioisosterism: A Rational Approach in Drug Design" Chem. Rev. 1996, 3176.

* cited by examiner

*Primary Examiner* — Joseph Kosack
(74) *Attorney, Agent, or Firm* — Lisa A. Dixon; Susan C. Kelly

(57) ABSTRACT

The present invention relates to compounds of formula I:

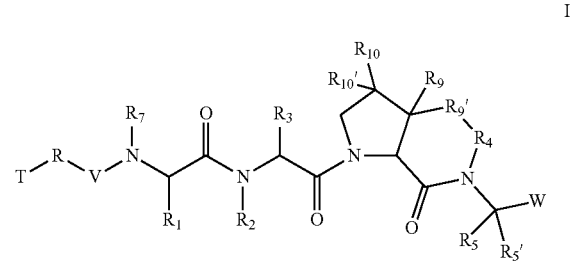

or a pharmaceutically acceptable salt, or mixtures thereof, that inhibit serine protease activity, particularly the activity of hepatitis C virus NS3-NS4A protease. As such, they act by interfering with the life cycle of the hepatitis C virus and are useful as antiviral agents. The invention further relates to pharmaceutically acceptable compositions comprising said compounds either for ex vivo use or for administration to a patient suffering from HCV infection and processes for preparing the compounds. The invention also relates to methods of treating an HCV infection in a patient by administering a pharmaceutical composition comprising a compound of this invention.

13 Claims, No Drawings

INHIBITORS OF SERINE PROTEASES, PARTICULARLY HCV NS3-NS4A PROTEASES

CROSS REFERENCE TO RELATED APPLICATIONS

The present application is a continuation application of U.S. application Ser. No. 12/169,209, filed on Jul. 8, 2008, entitled "Inhibitors of Serine Proteases, Particularly HCV NS3-NS4A Protease", which is a continuation application of U.S. patent application Ser. No. 10/821,793, filed Apr. 9, 2004, entitled "Inhibitors of Serine Proteases, Particularly HCV NS3-NS4A Protease", which in turn claims the benefit of U.S. Provisional Application No. 60/513,765, filed Oct. 23, 2003, entitled "Inhibitors of Serine Proteases, Particularly HCV NS3-NS4A Protease", the entire contents of each of which are hereby incorporated by reference.

TECHNICAL FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to pharmaceutical compositions comprising these compounds either for ex vivo use or for administration to a patient suffering from HCV infection. The invention also relates to processes for preparing the compounds and methods of treating an HCV infection in a patient by administering a pharmaceutical composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," *J. Hepatology*, 31. (Suppl. 1), pp. 17-24 (1999)]. Nearly four million individuals may be infected in the United States alone [M. J. Alter et al., "The Epidemiology of Viral Hepatitis in the United States, *Gastroenterol. Clin. North Am.*, 23, pp. 437-455 (1994); M. J. Alter "Hepatitis C Virus Infection in the United States," *J. Hepatology*, 31. (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews*, 14, pp. 201-204 (1994); D. Lavanchy, "Global Surveillance and Control of Hepatitis C," *J. Viral Hepatitis*, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211-220 (1994); I. Saito et. al., "Hepatitis C Virus Infection is Associated with the Development of Hepatocellular Carcinoma," *Proc. Natl. Acad. Sci. USA*, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." *Proc. Natl. Acad. Sci. USA*, 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524-9528 (1990); A. Takamizawa et. al., "Structure and Organization of the Hepatitis C Virus Genome Isolated From Human Carriers," *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," *J. Virol.*, 67, pp. 3835-3844 (1993); A. Grakoui et. al., "Characterization of the Hepatitis C Virus-Encoded Serine Proteinase: Determination of Proteinase-Dependent Polyprotein Cleavage Sites," *J. Virol.*, 67, pp. 2832-2843 (1993); A. Grakoui et. al., "Expression and Identification of Hepatitis C Virus Polyprotein Cleavage Products," *J. Virol.*, 67, pp. 1385-1395 (1993); L. Tomei et. al., "NS3 is a serine protease required for processing of hepatitis C virus polyprotein", *J. Virol.*, 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man, indicating that interrupting this stage of the viral life cycle results in therapeutically active agents. Consequently HCV NS3 serine protease is also an attractive target for drug discovery.

Furthermore, the current understanding of HCV has not led to any other satisfactory anti-HCV agents or treatments. Until recently, the only established therapy for HCV disease was interferon treatment. However, interferons have significant side effects [M. A. Wlaker et al., "Hepatitis C Virus: An Overview of Current Approaches and Progress," *DDT*, 4, pp. 518-29 (1999); D. Moradpour et al., "Current and Evolving Therapies for Hepatitis C," *Eur. J. Gastroenterol. Hepatol.*, 11, pp. 1199-1202 (1999); H. L. A. Janssen et al. "Suicide Associated with Alfa-Interferon Therapy for Chronic Viral Hepatitis," *J. Hepatol.*, 21, pp. 241-243 (1994); P. F. Renault et al., "Side Effects of Alpha Interferon," *Seminars in Liver Disease*, 9, pp. 273-277. (1989)] and induce long term remission in only a fraction (~25%) of cases [O. Weiland, "Interferon Therapy in Chronic Hepatitis C Virus Infection", *FEMS Microbiol. Rev.*, 14, pp. 279-288 (1994)]. Recent introductions of the pegylated forms of interferon (PEG-Intron® and Pegasys®) and the combination therapy of ribavirin and pegylated interferon (Rebetrol®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention provides a compound of formula I:

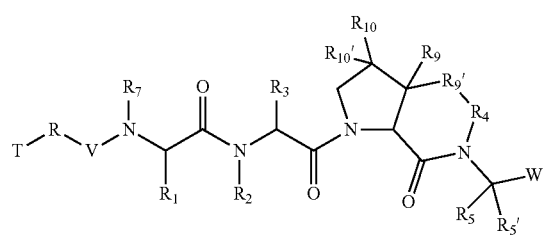

I or a pharmaceutically acceptable salt, or mixtures thereof, wherein:
W is:

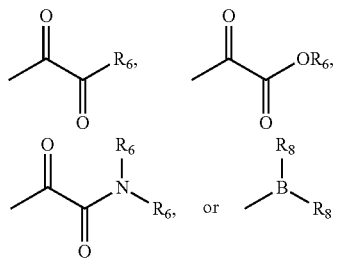

wherein each $R_6$ is independently:
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-, or
wherein up to 3 aliphatic carbon atoms in each $R_6$ may be optionally replaced with S, —S(O)—, —S(O)$_2$—, —O—, —N—, or —N(H)— in a chemically stable arrangement;
wherein $R_6$ may be optionally substituted with up to 3 J substituents; or
two $R_6$ groups, together with the nitrogen atom to which they are bound, may optionally form a 5- to 6-membered aromatic or a 3- to 7-membered saturated or partially unsaturated ring system wherein up to 3 ring atoms may be optionally replaced with N, NH, O, S, SO, and SO$_2$, wherein said ring system may be optionally fused to a (C6-C10)aryl, (C5-C10)het-eroaryl, (C3-C10)cycloalkyl, or a (C3-C10)heterocyclyl, wherein any ring has up to 3 substituents selected independently from J;
wherein each $R_8$ is independently —OR'; or the $R_8$ groups together with the boron atom, may optionally form a (C3-C10)-membered heterocyclic ring having, in addition to the boron, up to 3 ring atoms optionally replaced with N, NH, O, S, SO, and SO$_2$;
J is halogen, —OR', —NO$_2$, —CN, —CF$_3$, —OCF$_3$, —R', oxo, thioxo, =N(R'), =N(OR'), 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)C(O)OR', —C(O)C(O)NR', —C(O)CH$_2$C(O)R', —C(S)R', —C(S)OR', —C(O)OR', —OC(O)R', —C(O)N (R')$_2$, —OC(O)N(R')$_2$, —C(S)N(R')$_2$, —(CH$_2$)$_{0-2}$NHC(O) R', —N(R')N(R')COR', —N(R')N(R')C(O)OR', —N(R')N (R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR') COR', —N(OR')R', —C(=NH)N(R')$_2$, —C(O)N(OR')R', —C(=NOR')R', —OP(O)(OR')$_2$, —P(O)(R')$_2$, —P(O) (OR')$_2$, or —P(O)(H)(OR'); wherein;
R' is independently selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' may be optionally and independently substituted with J;
wherein two R' groups bound to the same atom may optionally form a 5- to 6-membered aromatic or a 3- to 7-membered saturated or partially unsaturated ring system wherein up to 3 ring atoms may be optionally replaced with a heteroatom independently selected from N, NH, O, S, SO, and SO$_2$, wherein said ring system may be optionally fused to a (C6-C10)aryl, (C5-C10)heteroaryl, (C3-C10)cycloalkyl, or a (C3-C10)heterocyclyl, wherein any ring has up to 3 substituents selected independently from J;
$R_5$ and $R_{5'}$ are each independently hydrogen or (C1-C12)-aliphatic, wherein any hydrogen may be optionally replaced with halogen; wherein any terminal carbon atom of $R_5$ may be optionally substituted with sulfhydryl or hydroxy; or $R_5$ is Ph or —CH$_2$Ph and $R_{5'}$ is H, wherein said Ph or —CH$_2$Ph group may be optionally substituted with up to 3 substituents independently selected from J; or
$R_5$ and $R_{5'}$ together with the atom to which they are bound may optionally form a 3- to 6-membered saturated or partially unsaturated ring system wherein up to 2 ring atoms may be optionally replaced with N, NH, O, SO, or SO$_2$; wherein said ring system has up to 2 substituents selected independently from J;
$R_2$, $R_4$, and $R_7$ are each independently:
hydrogen-,
(C1-C12)-aliphatic-,
(C3-C10)-cycloalkyl-(C1-C12)-aliphatic-, or
(C6-C10)-aryl-(C1-C12)-aliphatic-;
wherein up to two aliphatic carbon atoms in each of $R_2$, $R_4$, and $R_7$ may be optionally replaced with S, —S(O)—, —S(O)$_2$—, —O—, —N—, or —N(H)— in a chemically stable arrangement;

wherein each of R$_2$, R$_4$, and R$_7$ may be independently and optionally substituted with up to 3 substituents independently selected from J;

R$_1$ and R$_3$ are each independently:
- (C1-C12)-aliphatic-,
- (C3-C10)-cycloalkyl- or -cycloalkenyl-,
- [(C3-C10)-cycloalkyl- or -cycloalkenyl]-(C1-C12)-aliphatic-,
- (C6-C10)-aryl-(C1-C12)aliphatic-, or
- (C5-C10)-heteroaryl-(C1-C12)-aliphatic-;
    wherein up to 3 aliphatic carbon atoms in each of R$_1$ and R$_3$ may be optionally replaced with S, —S(O)—, —S(O)$_2$—, —O—, —N—, or —N(H)— in a chemically stable arrangement;
    wherein each of R$_1$ and R$_3$ may be independently and optionally substituted with up to 3 substituents independently selected from J;

R$_9$, R$_{9'}$, R$_{10}$, and R$_{10'}$ are each independently —X—Y—Z;

X is a bond, —C(H)(R$_6$)—, —O—, —S—, or —N(R$_{11}$)—;

R$_{11}$ is:
- hydrogen-,
- (C1-C12)-aliphatic-,
- (C6-C10)-aryl-,
- (C6-C10)-aryl-(C1-C12)aliphatic-,
- (C3-C10)-cycloalkyl- or cycloalkenyl-,
- [(C3-C10)-cycloalkyl- or cycloalkenyl]-(C1-C12)-aliphatic-,
- (C3-C10)-heterocyclyl-,
- (C3-C10)-heterocyclyl-(C1-C12)-aliphatic-,
- (C5-C10)-heteroaryl-, or
- (C5-C10)-heteroaryl-(C1-C12)-aliphatic-,
    wherein up to 3 aliphatic carbon atoms in each R$_{11}$ may be optionally replaced with S, —S(O)—, —S(O)$_2$—, —O—, —N—, or —N(H)— in a chemically stable arrangement;
    wherein R$_{11}$ may be optionally substituted with up to 3 J substituents; or
    wherein R$_{11}$ and Z together with the atoms to which they are bound, optionally form a nitrogen containing 5-7-membered mono- or 6-11-membered bicyclic ring system optionally substituted with up to 3 J substitutents, wherein up to 3 ring atoms in said ring system may be optionally replaced with O, NH, S, SO, or SO$_2$ in a chemically stable arrangement;

Y is a bond, —CH$_2$—, —C(O)—, —C(O)C(O)—, —S(O)—, S(O)$_2$—, or —S(O)(NR$_{12}$)—;

R$_{12}$ is:
- hydrogen-,
- (C1-C12)-aliphatic-,
- (C6-C10)-aryl-,
- (C6-C10)-aryl-(C1-C12)aliphatic-,
- (C3-C10)-cycloalkyl- or cycloalkenyl-,
- [(C3-C10)-cycloalkyl- or cycloalkenyl]-(C1-C12)-aliphatic-,
- (C3-C10)-heterocyclyl-,
- (C3-C10)-heterocyclyl-(C1-C12)-aliphatic-,
- (C5-C10)-heteroaryl-, or
- (C5-C10)-heteroaryl-(C1-C12)-aliphatic-,
    wherein up to 3 aliphatic carbon atoms in each R$_{12}$ may be optionally replaced with S, —S(O)—, —S(O)$_2$—, —O—, —N—, or —N(H)—, in a chemically stable arrangement;
    wherein R$_{12}$ may be optionally substituted with up to 3 J substituents;

Z is:
- hydrogen-,
- (C1-C12)-aliphatic-,
- (C3-C10)-cycloalkyl- or -cycloalkenyl-,
- [(C3-C10)-cycloalkyl or -cycloalkenyl]-(C1-C12)-aliphatic-,
- (C6-C10)-aryl-,
- (C6-C10)-aryl-(C1-C12)aliphatic-,
- (C3-C10)-heterocyclyl-,
- (C3-C10)-heterocyclyl-(C1-C12)aliphatic-,
- (C5-C10)-heteroaryl-, or
- (C5-C10)-heteroaryl-(C1-C12)-aliphatic-;
    wherein up to three aliphatic carbon atoms in Z may be optionally replaced with S, —S(O)—, —S(O)$_2$—, —O—, —N—, or —N(H)—, in a chemically stable arrangement;
    wherein any ring may be optionally fused to a (C6-C10) aryl, (C5-C10)heteroaryl, (C3-C10)cycloalkyl, or (C3-C10)heterocyclyl;
    wherein Z may be independently and optionally substituted with up to 3 substituents independently selected from J;

V is —C(O)—, —S(O)—, or —S(O)$_2$—;

R is —C(O)—, —S(O)—, —S(O)$_2$—, —N(R$_{12}$)—, —O—, or a bond;

T is:
- (C1-C12)-aliphatic-;
- (C6-C10)-aryl-,
- (C6-C10)-aryl-(C1-C12)aliphatic-,
- (C3-C10)-cycloalkyl or -cycloalkenyl-,
- [(C3-C10)-cycloalkyl or -cycloalkenyl]-(C1-C12)-aliphatic-,
- (C3-C10)-heterocyclyl-,
- (C3-C10)-heterocyclyl-(C1-C12)-aliphatic-,
- (C5-C10)-heteroaryl-, or
- (C5-C10)-heteroaryl-(C1-C12)-aliphatic-;
    wherein up to 3 aliphatic carbon atoms in T may be replaced with S, —S(O)—, —S(O)$_2$—, —O—, —N—, or —N(H)—, in a chemically stable arrangement;
    wherein each T may be optionally substituted with up to 3 J substituents; or T is selected from —N(R$_6$)(R$_{6'}$); and R$_{6'}$ is
- hydrogen-,
- (C1-C12)-aliphatic-,
- (C6-C10)-aryl-,
- (C6-C10)-aryl-(C1-C12)aliphatic-,
- (C3-C10)-cycloalkyl- or cycloalkenyl-,
- [(C3-C10)-cycloalkyl- or cycloalkenyl]-(C1-C12)-aliphatic-,
- (C3-C10)-heterocyclyl-,
- (C3-C10)-heterocyclyl-(C1-C12)-aliphatic-,
- (C5-C10)-heteroaryl-, or
- (C5-C10)-heteroaryl-(C1-C12)-aliphatic-, or
    wherein up to 3 aliphatic carbon atoms in each R$_{6'}$ may be optionally replaced with S, —S(O)—, —S(O)$_2$—, —O—, —N—, or —N(H)— in a chemically stable arrangement;
    wherein R$_{6'}$ may be optionally substituted with up to 3 J substituents; or
    R$_6$ and R$_{6'}$, together with the nitrogen atom to which they are bound, may optionally form a (C3-C10)-heterocyclic ring system wherein said ring system may be optionally substituted with up to 3 substituents independently selected from J.

The invention also relates to processes for preparing the above compounds and to compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

DETAILED DESCRIPTION OF THE INVENTION

The present invention provides a compound of formula I:

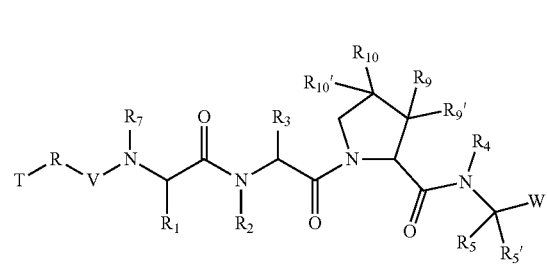

I or a pharmaceutically acceptable salt, or mixtures thereof, wherein:
W is:

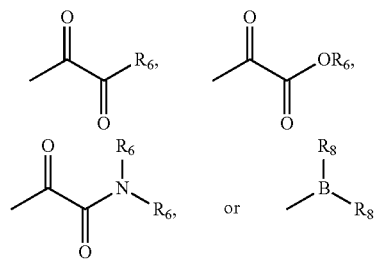

wherein each $R_6$ is independently:
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-, or
wherein up to 3 aliphatic carbon atoms in each $R_6$ may be optionally replaced with S, —S(O)—, —S(O)$_2$—, —O—, —N—, or —N(H)— in a chemically stable arrangement;
wherein $R_6$ may be optionally substituted with up to 3 J substituents; or
two $R_6$ groups, together with the nitrogen atom to which they are bound, may optionally form a 5- to 6-membered aromatic or a 3- to 7-membered saturated or partially unsaturated ring system wherein up to 3 ring atoms may be optionally replaced with N, NH, O, S, SO, and SO$_2$, wherein said ring system may be optionally fused to a (C6-C10)aryl, (C5-C10)het-eroaryl, (C3-C10)cycloalkyl, or a (C3-C10)heterocyclyl, wherein any ring has up to 3 substituents selected independently from J;
wherein each $R_8$ is independently —OR'; or the $R_8$ groups together with the boron atom, may optionally form a (C3-C10)-membered heterocyclic ring having, in addition to the boron, up to 3 ring atoms optionally replaced with N, NH, O, S, SO, and SO$_2$;
J is halogen, —OR', —NO$_2$, —CN, —CF$_3$, —OCF$_3$, —R', oxo, thioxo, =N(R'), =N(OR'), 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)C(O)OR', —C(O)C(O)NR', —C(O)CH$_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —OP(O)(R')$_2$, —P(O)(OR')$_2$, or —P(O)(H)(OR'); wherein;
R' is independently selected from:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, and
(C5-C10)-heteroaryl-(C1-C12)-aliphatic-;
wherein up to 5 atoms in R' may be optionally and independently substituted with J;
wherein two R' groups bound to the same atom may optionally form a 5- to 6-membered aromatic or a 3- to 7-membered saturated or partially unsaturated ring system wherein up to 3 ring atoms may be optionally replaced with a heteroatom independently selected from N, NH, O, S, SO, and SO$_2$, wherein said ring system may be optionally fused to a (C6-C10)aryl, (C5-C10)heteroaryl, (C3-C10)cycloalkyl, or a (C3-C10)heterocyclyl, wherein any ring has up to 3 substituents selected independently from J;
$R_5$ and $R_{5'}$ are each independently hydrogen or (C1-C12)-aliphatic, wherein any hydrogen may be optionally replaced with halogen; wherein any terminal carbon atom of $R_5$ may be optionally substituted with sulfhydryl or hydroxy; or $R_5$ is Ph or —CH$_2$Ph and $R_{5'}$ is H, wherein said Ph or —CH$_2$Ph group may be optionally substituted with up to 3 substituents independently selected from J; or
$R_5$ and $R_{5'}$ together with the atom to which they are bound may optionally form a 3- to 6-membered saturated or partially unsaturated ring system wherein up to 2 ring atoms may be optionally replaced with N, NH, O, SO, or SO$_2$; wherein said ring system has up to 2 substituents selected independently from J;
$R_2$, $R_4$, and $R_7$ are each independently:
hydrogen-,
(C1-C12)-aliphatic-,
(C3-C10)-cycloalkyl-(C1-C12)-aliphatic-, or
(C6-C10)-aryl-(C1-C12)-aliphatic-;
wherein up to two aliphatic carbon atoms in each of $R_2$, $R_4$, and $R_7$ may be optionally replaced with S, —S(O)—, —S(O)$_2$—, —O—, —N—, or —N(H)— in a chemically stable arrangement;
wherein each of $R_2$, $R_4$, and $R_7$ may be independently and optionally substituted with up to 3 substituents independently selected from J;

$R_1$ and $R_3$ are each independently:
(C1-C12)-aliphatic-,
(C3-C10)-cycloalkyl- or -cycloalkenyl-,
[(C3-C10)-cycloalkyl- or -cycloalkenyl]-(C1-C12)-aliphatic-,
(C6-C10)-aryl-(C1-C12)aliphatic-, or
(C5-C10)-heteroaryl-(C1-C12)-aliphatic-;
wherein up to 3 aliphatic carbon atoms in each of $R_1$ and $R_3$ may be optionally replaced with S, —S(O)—, —S(O)$_2$—, —O—, —N—, or —N(H)— in a chemically stable arrangement;
wherein each of $R_1$ and $R_3$ may be independently and optionally substituted with up to 3 substituents independently selected from J;

$R_9$, $R_{9'}$, $R_{10}$, and $R_{10'}$ are each independently —X—Y—Z;
X is a bond, —C(H)($R_6$)—, —O—, —S—, or —N($R_{11}$)—;
$R_{11}$ is:
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-,
wherein up to 3 aliphatic carbon atoms in each $R_{11}$ may be optionally replaced with S, —S(O)—, —S(O)$_2$—, —O—, —N—, or —N(H)— in a chemically stable arrangement;
wherein $R_{11}$ may be optionally substituted with up to 3 J substituents; or
wherein $R_{11}$ and Z together with the atoms to which they are bound, optionally form a nitrogen containing 5-7-membered mono- or 6-11-membered bicyclic ring system optionally substituted with up to 3 J substitutents, wherein up to 3 ring atoms in said ring system may be optionally replaced with O, NH, S, SO, or SO$_2$ in a chemically stable arrangement;

Y is a bond, —CH$_2$—, —C(O)—, —C(O)C(O)—, —S(O)—, S(O)$_2$—, or —S(O)(NR$_{12}$)—;
$R_{12}$ is:
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-,
wherein up to 3 aliphatic carbon atoms in each $R_{12}$ may be optionally replaced with S, —S(O)—, —S(O)$_2$—, —O—, —N—, or —N(H)—, in a chemically stable arrangement;
wherein $R_{12}$ may be optionally substituted with up to 3 J substituents;

Z is:
hydrogen-,
(C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or
(C5-C10)-heteroaryl-(C1-C12)-aliphatic-;
wherein up to three aliphatic carbon atoms in Z may be optionally replaced with S, —S(O)—, —S(O)$_2$—, —O—, —N—, or —N(H)—, in a chemically stable arrangement;
wherein any ring may be optionally fused to a (C6-C10) aryl, (C5-C10)heteroaryl, (C3-C10)cycloalkyl, or (C3-C10)heterocyclyl;
wherein Z may be independently and optionally substituted with up to 3 substituents independently selected from J;

V is —C(O)—, —S(O)—, or —S(O)$_2$—;
R is —C(O)—, —S(O)—, —S(O)$_2$—, —N(R$_{12}$)—, —O—, or a bond;
T is:
(C1-C12)-aliphatic-;
(C6-C10)-aryl-,
(C6-C10)-aryl-(C1-C12)aliphatic-,
(C3-C10)-cycloalkyl or -cycloalkenyl-,
[(C3-C10)-cycloalkyl or -cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-;
wherein up to 3 aliphatic carbon atoms in T may be replaced with S, —S(O)—, —S(O)$_2$—, —O—, —N—, or —N(H)—, in a chemically stable arrangement;
wherein each T may be optionally substituted with up to 3 J substituents; or
T is selected from —N(R$_6$)(R$_{6'}$); and
$R_{6'}$ is
hydrogen-,
(C1-C12)-aliphatic-,
(C6-C10)-aryl-,
(C6-C10)-aryl-(C1-C12)aliphatic-,
(C3-C10)-cycloalkyl- or cycloalkenyl-,
[(C3-C10)-cycloalkyl- or cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-, or
wherein up to 3 aliphatic carbon atoms in each $R_{6'}$ may be optionally replaced with S, —S(O)—, —S(O)$_2$—, —O—, —N—, or —N(H)— in a chemically stable arrangement;
wherein $R_{6'}$ may be optionally substituted with up to 3 J substituents; or
$R_6$ and $R_{6'}$, together with the nitrogen atom to which they are bound, may optionally form a (C3-C10)-heterocyclic ring system wherein said ring system may be optionally substituted with up to 3 substituents independently selected from J.

DEFINITIONS

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin. It is understood that as used herein, the term "(C6-C10)-aryl-" includes any one of a C6, C7, C8, C9, and C10 monocyclic or bicyclic carbocyclic aromatic ring.

The term "heterocyclyl" as used herein means a monocyclic or bicyclic non-aromatic ring system having 1 to 3 heteroatom or heteroatom groups in each ring selected from O, N, NH, S, SO, and $SO_2$ in a chemically stable arrangement. In a bicyclic non-aromatic ring system embodiment of "heterocyclyl" one or both rings may contain said heteroatom or heteroatom groups. It is understood that as used herein, the term "(C5-C10)-heterocyclyl-" includes any one of a C5, C6, C7, C8, C9, and C10 monocyclic or bicyclic non-aromatic ring system having 1 to 3 heteroatom or heteroatom groups in each ring selected from O, N, NH, and S in a chemically stable arrangement.

The term "heteroaryl" as used herein means a monocyclic or bicyclic aromatic ring system having 1 to 3 heteroatom or heteroatom groups in each ring selected from O, N, NH, and S in a chemically stable arrangement. In such a bicyclic aromatic ring system embodiment of "heteroaryl":
one or both rings may be aromatic; and
one or both rings may contain said heteroatom or heteroatom groups. It is understood that as used herein, the term "(C5-C10)-heteroaryl-" includes any one of a C5, C6, C7, C8, C9, and C10 monocyclic or bicyclic aromatic ring system having 1 to 3 heteroatom or heteroatom groups in each ring selected from O, N, NH, and S in a chemically stable arrangement.

The term "aliphatic" as used herein means a straight chained or branched alkyl, alkenyl or alkynyl. It is understood that as used herein, the term "(C1-C12)-aliphatic-" includes any one of a C1, C2, C3, C4, C5, C6, C7, C8, C9, C10, C11, and C12 straight or branched alkyl chain of carbon atoms. It is also understood that alkenyl or alkynyl embodiments need at least two carbon atoms in the aliphatic chain. The term "cycloalkyl or cycloalkenyl" refers to a monocyclic or fused or bridged bicyclic carbocyclic ring system that is not aromatic. Cycloalkenyl rings have one or more units of unsaturation. It is also understood that as used herein, the term "(C3-C10)-cycloalkyl- or -cycloalkenyl-" includes any one of a C3, C4, C5, C6, C7, C8, C9, and C10 monocyclic or fused or bridged bicyclic carbocyclic ring. Preferred cycloalkyl groups include cyclopropyl, cyclobutyl, cyclopentyl, cyclohexyl, cyclohexenyl, cycloheptyl, cycloheptenyl, nornbornyl, adamantyl and decalin-yl.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

EMBODIMENTS

According to one embodiment of compounds of formula I, the

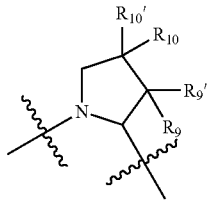

radical is,

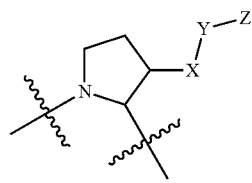

wherein;
in $R_9$, $R_{10}$, and $R_{10'}$, X and Y are both a bond and Z is hydrogen; and in $R_{9'}$;
X is a bond;
Y is a bond, —$CH_2$—, or —C(O)—; and
Z is (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C3-C10)-heterocyclyl-(C1-C12)aliphatic-,
  (C5-C10)-heteroaryl-, or
  (C5-C10)-heteroaryl-(C1-C12)-aliphatic-;
    wherein up to three aliphatic carbon atoms in Z may be optionally replaced with S, —S(O)—, —S(O)$_2$—, —O—, —N—, or —N(H)—, in a chemically stable arrangement;
    wherein any ring may be optionally fused to a (C6-C10) aryl, (C5-C10)heteroaryl, (C3-C10)cycloalkyl, or (C3-C10)heterocyclyl;
    wherein Z may be independently and optionally substituted with up to 3 substituents independently selected from J.
According to another embodiment, in $R_{9'}$;
X is a bond;
Y is a bond; and
Z is (C1-C12)-aliphatic-,
  (C3-C10)-cycloalkyl- or -cycloalkenyl-,
  [(C3-C10)-cycloalkyl or -cycloalkenyl]-(C1-C12)-aliphatic-,
  (C6-C10)-aryl-,
  (C6-C10)-aryl-(C1-C12)aliphatic-,
  (C5-C10)-heteroaryl-, or
  (C5-C10)-heteroaryl-(C1-C12)-aliphatic-;
    wherein up to three aliphatic carbon atoms in Z may be optionally replaced with S, —S(O)—, —S(O)$_2$—, —O—, —N—, or —N(H)—, in a chemically stable arrangement;

wherein any ring may be optionally fused to a (C6-C10) aryl, (C5-C10)heteroaryl, (C3-C10)cycloalkyl, or (C3-C10)heterocyclyl;
wherein Z may be independently and optionally substituted with up to 3 substituents independently selected from J.

According to another embodiment, in $R_{9'}$;
X is a bond;
Y is a bond; and
Z is (C1-C12)-aliphatic-,
(C3-C10)-cycloalkyl- or -cycloalkenyl-,
[(C3-C10)-cycloalkyl or -cycloalkenyl]-(C1-C12)-aliphatic-, or
(C6-C10)-aryl-(C1-C12)aliphatic-,
wherein up to three aliphatic carbon atoms in Z may be optionally replaced with S, —S(O)—, —S(O)$_2$—, —O—, —N—, or —N(H)—, in a chemically stable arrangement;
wherein Z may be independently and optionally substituted with up to 3 substituents independently selected from J.

According to another embodiment, $R_{9'}$ is

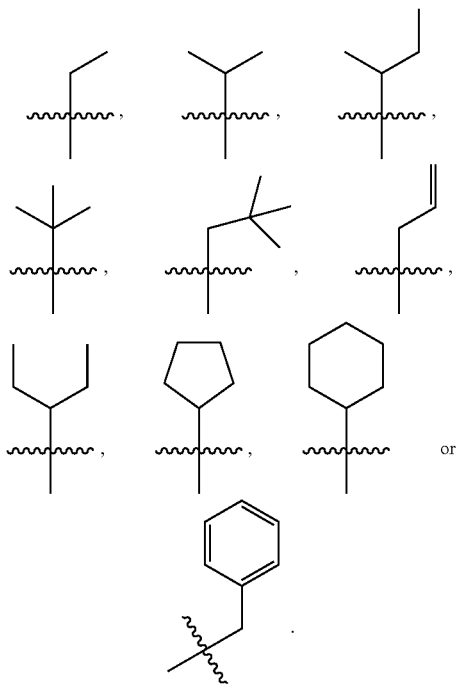

According to another embodiment, $R_{9'}$ is

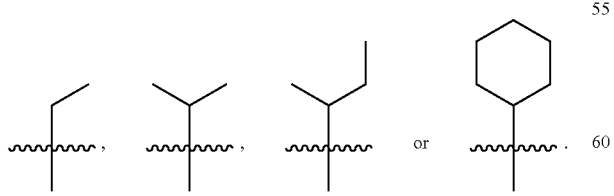

According to another embodiment, $R_{9'}$ is ethyl.
According to another embodiment of compounds of formula I, in $R_9$, $R_{10}$, and $R_{10'}$, X and Y are both a bond and Z is hydrogen; and in $R_{9'}$;

X is a bond;
Y is —C(O)—; and
Z is (C1-C12)-aliphatic-, or
(C3-C10)-heterocyclyl-(C1-C12)aliphatic-;
wherein up to three aliphatic carbon atoms in Z may be optionally replaced with S, —S(O)—, —S(O)$_2$—, —O—, —N—, or —N(H)—, in a chemically stable arrangement;
wherein any ring may be optionally fused to a (C6-C10) aryl, (C5-C10)heteroaryl, (C3-C10)cycloalkyl, or (C3-C10)heterocyclyl;
wherein Z may be independently and optionally substituted with up to 3 substituents independently selected from J.

According to another embodiment, Z is —O—(C1-C6)-aliphatic or —N(R')$_2$, wherein the two R' groups bound to the nitrogen atom may optionally form a 3- to 7-membered saturated or partially unsaturated ring system wherein up to 3 ring atoms may be optionally replaced with a heteroatom independently selected from N, NH, O, S, SO, and SO$_2$, wherein said ring system may be optionally fused to a (C6-C10)aryl, (C5-C10)heteroaryl, (C3-C10)cycloalkyl, or a (C3-C10)heterocyclyl, wherein any ring has up to 3 substituents selected independently from J.

According to another embodiment of compounds of formula I, Z is —N(R')$_2$, wherein the two R' groups bound to the nitrogen atom may optionally form a 3- to 7-membered saturated or partially unsaturated ring system wherein up to 3 ring atoms may be optionally replaced with a heteroatom independently selected from N, NH, O, S, SO, and SO$_2$, wherein said ring system may be optionally fused to a (C6-C10)aryl, (C5-C10)heteroaryl, (C3-C10)cycloalkyl, or a (C3-C10)heterocyclyl, wherein any ring has up to 3 substituents selected independently from J.

According to another embodiment of compounds of formula I, in $R_9$, and $R_{10}$, X and Y are both a bond and Z is hydrogen; and in each of $R_{9'}$ and $R_{10'}$, independently,
X is a bond;
Y is a bond; and
Z is (C1-C12)-aliphatic-,
(C3-C10)-cycloalkyl- or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)aliphatic-,
(C5-C10)-heteroaryl-, or
(C5-C10)-heteroaryl-(C1-C12)-aliphatic-;
wherein up to three aliphatic carbon atoms in Z may be optionally replaced with S, —S(O)—, —S(O)$_2$—, —O—, —N—, or —N(H)—, in a chemically stable arrangement;
wherein any ring may be optionally fused to a (C6-C10) aryl, (C5-C10)heteroaryl, (C3-C10)cycloalkyl, or (C3-C10)heterocyclyl;
wherein Z may be independently and optionally substituted with up to 3 substituents independently selected from J.

According to another embodiment, Z in each of $R_{9'}$ and $R_{10'}$ independently, is
(C1-C12)-aliphatic-,
(C3-C10)-cycloalkyl- or -cycloalkenyl-, or
[(C3-C10)-cycloalkyl or -cycloalkenyl]-(C1-C12)-aliphatic-;

wherein up to three aliphatic carbon atoms in Z may be optionally replaced with S, —S(O)—, —S(O)₂—, —O—, —N—, or —N(H)—, in a chemically stable arrangement;

wherein Z may be independently and optionally substituted with up to 3 substituents independently selected from J.

According to another embodiment Z, in each of $R_9$, and $R_{10'}$, independently is (C1-C6)-aliphatic-.

According to another embodiment of compounds of formula I, in $R_{10}$, and $R_{10'}$, X and Y are both a bond and Z is hydrogen; and in $R_9$ and $R_{9'}$;

X is a bond,
Y is a bond, and
Z is (C1-C6)-aliphatic-,
wherein Z may be independently and optionally substituted with up to 3 substituents independently selected from J.

According to another embodiment of compounds of formula I, W is:

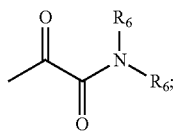

wherein in the W, the $NR_6R_6$ is selected from —NH—(C1-C6 aliphatic), —NH—(C3-C6 cycloalkyl), —NH—CH(CH₃)-aryl, or —NH—CH(CH₃)-heteroaryl, wherein said aryl or said heteroaryl is optionally substituted with up to 3 halogens.

According to another embodiment in the W, the $NR_6R_6$ is:

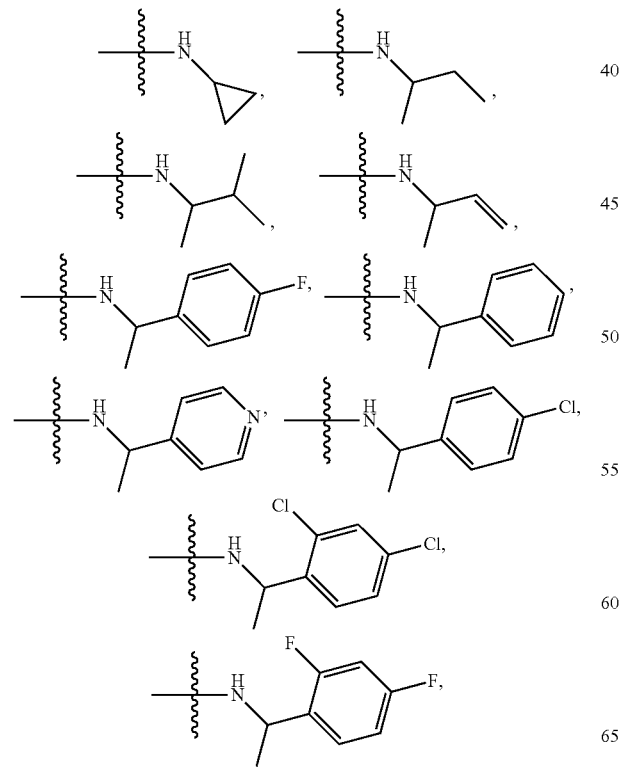

According to another embodiment in the W, the $NR_6R_6$ is:

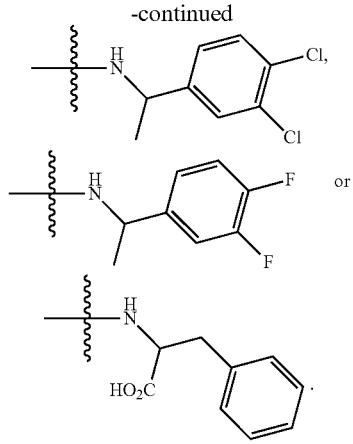

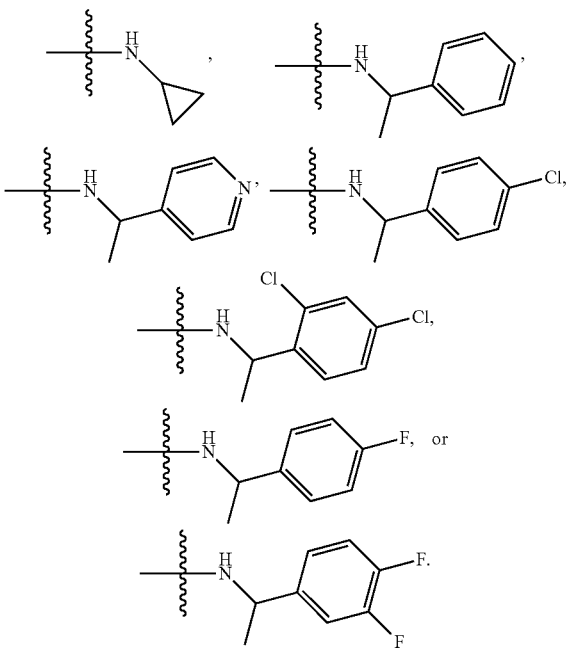

According to another embodiment in the W, the $NR_6R_6$ is:

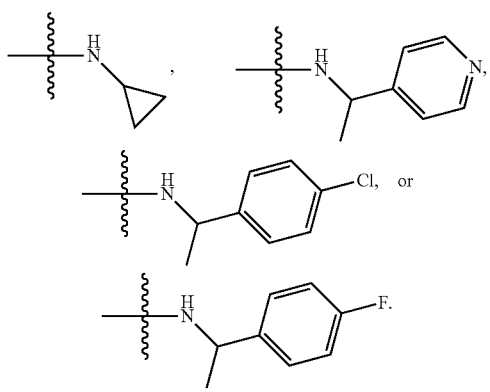

According to another embodiment in the W, the NR$_6$R$_6$ is:

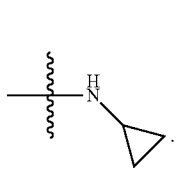 [SMILES: *NC1CC1]

According to another embodiment in compounds of formula I, the NR$_6$R$_6$ in the W radical is:

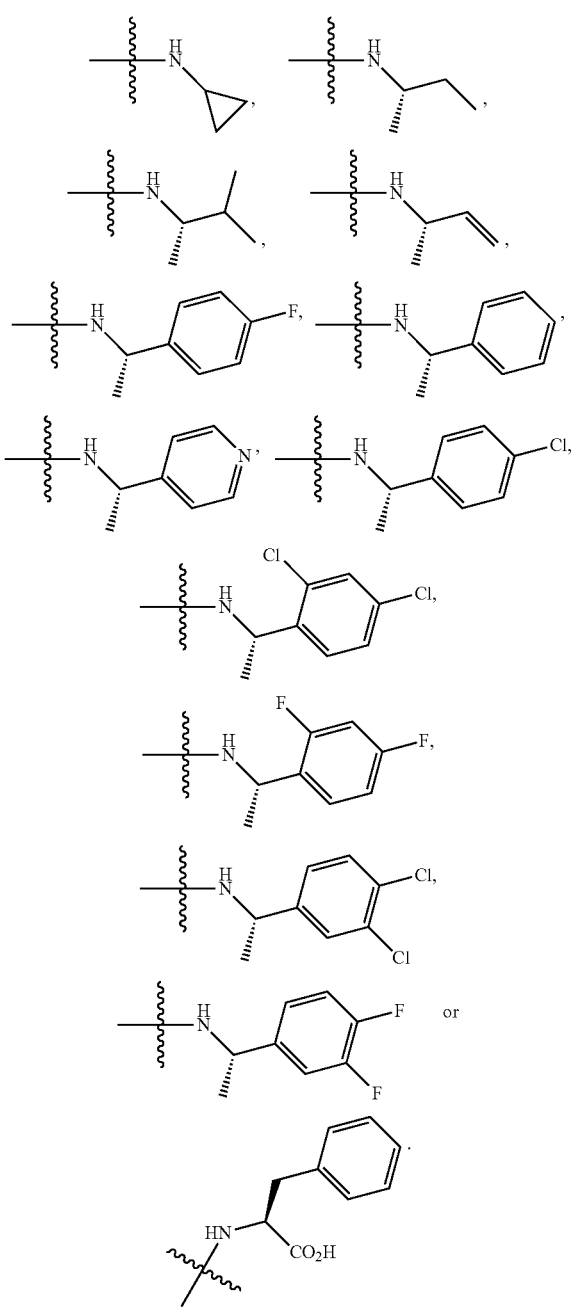

According to another embodiment, the NR$_6$R$_6$ in the W radical is:

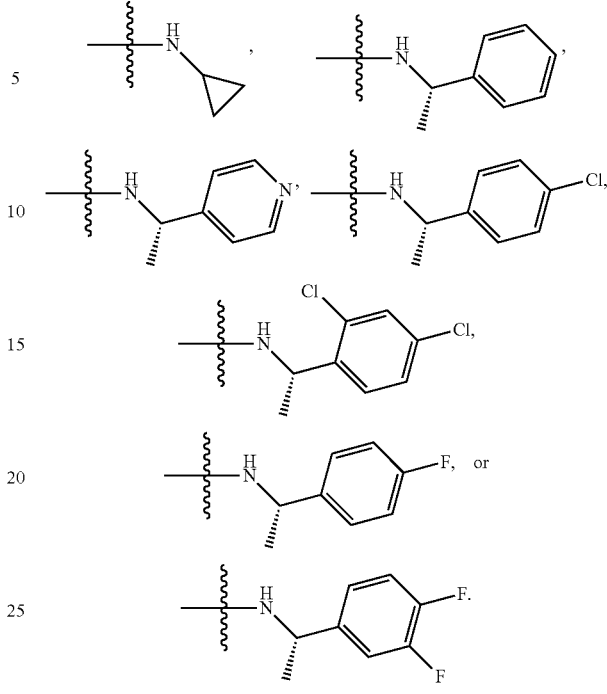

According to another embodiment, in the W, the NR$_6$R$_6$ is:

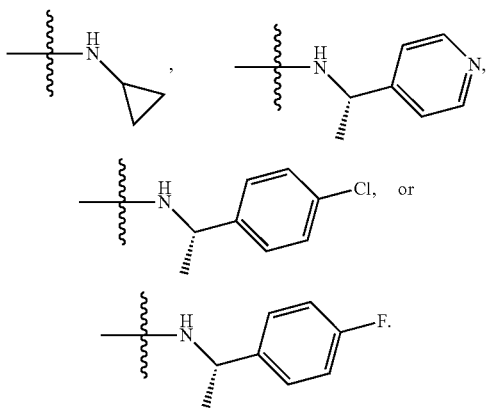

According to another embodiment W in compounds of formula I is:

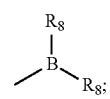

wherein R$_8$ is as defined above.

According to another embodiment each R$_8$ together with the boron atom, is a (C5-C10)-membered heterocyclic ring having no additional heteroatoms other than the boron and the two oxygen atoms.

In another embodiment W is:

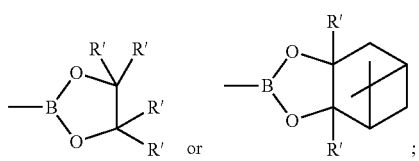

wherein R' is (C1-C6)-aliphatic.

In another embodiment R' is methyl.

According to another embodiment of compounds of formula I, $R_{5'}$ is hydrogen and $R_5$ is:

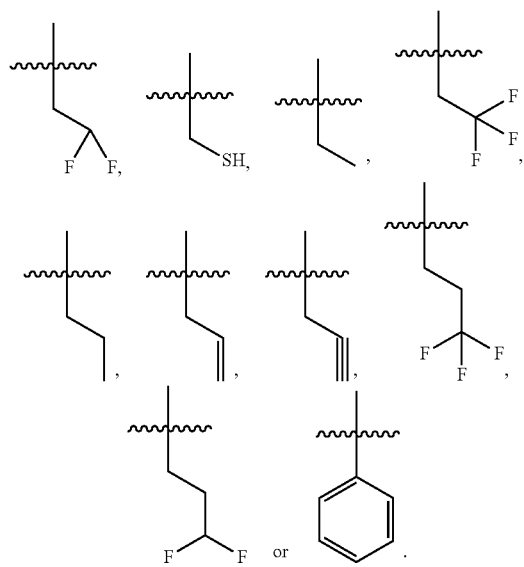

According to another embodiment $R_{5'}$ is hydrogen and $R_5$ is:

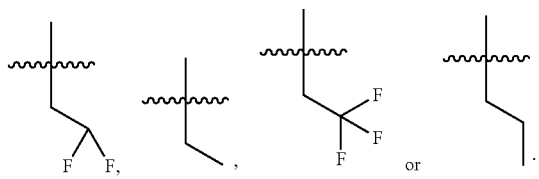

According to another embodiment in compounds of formula I, $R_{5'}$ and $R_5$ is:

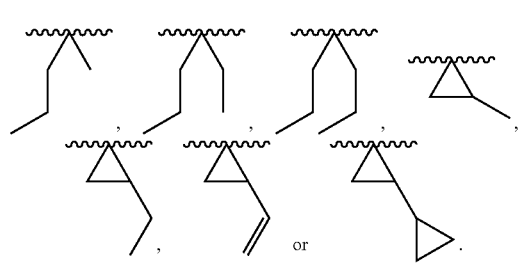

According to another embodiment of compounds of formula I, $R_2$, $R_4$, and $R_7$ are each independently H, methyl, ethyl, or propyl.

According to another embodiment $R_2$, $R_4$, and $R_7$ are each hydrogen.

According to another embodiment of compounds of formula I, $R_3$ is:

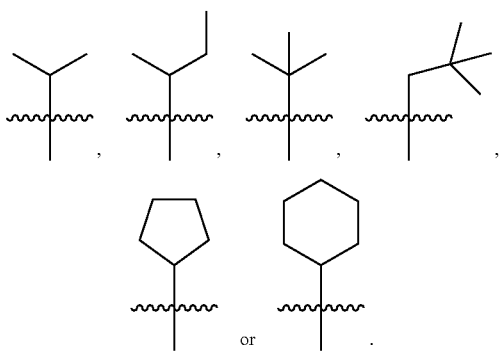

According to another embodiment $R_3$ is:

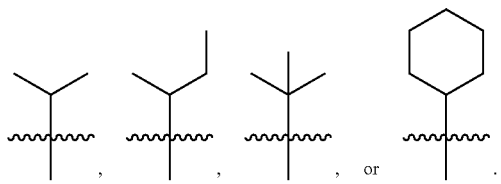

According to another embodiment $R_3$ is:

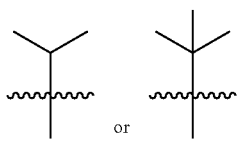

According to another embodiment of compounds of formula I, $R_1$ is:

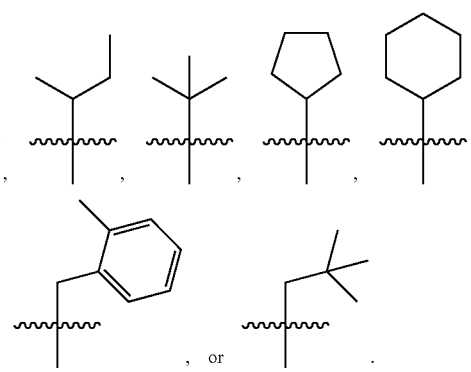

According to another embodiment R₁ is:

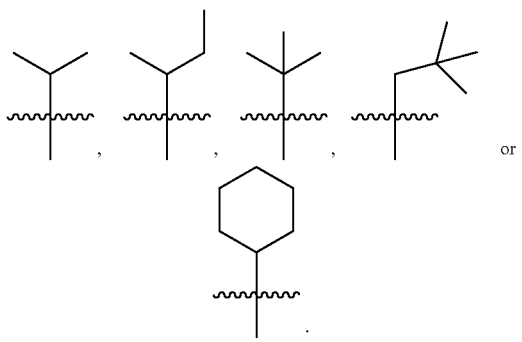

According to another embodiment wherein R₁ is isopropyl or cyclohexyl.

According to another embodiment of compounds of formula I, the

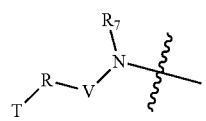

radical is:

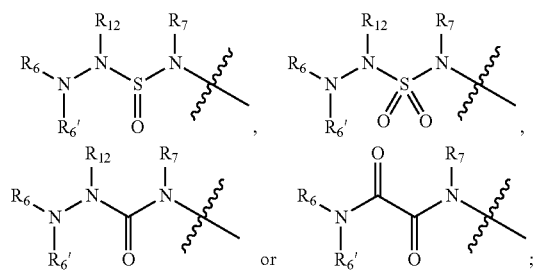

wherein:

R₆, R₆', R₇, and R₁₂, are as defined in any of the embodiments herein.

According to another embodiment in the

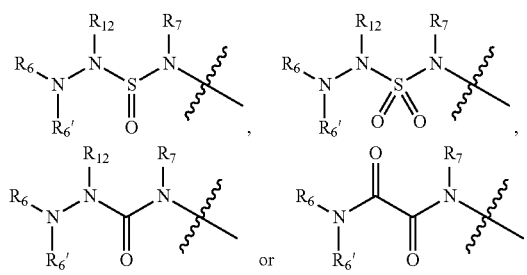

radical;

R₆' and R₇ are both hydrogen;
R₆ is:
(C1-C12)-aliphatic-;
(C6-C10)-aryl-,
(C6-C10)-aryl-(C1-C12)aliphatic-,
(C3-C10)-cycloalkyl or -cycloalkenyl-,
[(C3-C10)-cycloalkyl or -cycloalkenyl]-(C1-C12)-aliphatic-,
(C3-C10)-heterocyclyl-,
(C3-C10)-heterocyclyl-(C1-C12)-aliphatic-,
(C5-C10)-heteroaryl-, or
(C5-C10)-heteroaryl-(C1-C12)-aliphatic-;
  wherein up to 3 aliphatic carbon atoms in R₆ may be optionally replaced by S, —S(O)—, —S(O)₂—, —O—, —N—, or —N(H)—, in a chemically stable arrangement; and
  wherein R₆ may be optionally substituted with up to 3 substituents independently selected from J; and
R₁₂ is as defined in any of the embodiments herein.

According to another embodiment
R₆ is:
(C1-C12)-aliphatic-;
(C6-C10)-aryl-(C1-C12)aliphatic-, or
(C3-C10)-cycloalkyl or -cycloalkenyl-;
  wherein up to 3 aliphatic carbon atoms in R₆ may be optionally replaced by S, —S(O)—, —S(O)₂—, —O—, —N—, or —N(H)—, in a chemically stable arrangement;
  wherein R₆ may be optionally substituted with up to 3 substituents independently selected from J; and
R₁₂ is as defined in any of the embodiments herein.

According to another embodiment the radical is:

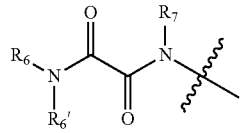

According to another embodiment the

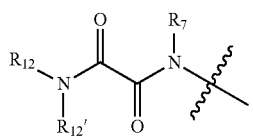

radical is:

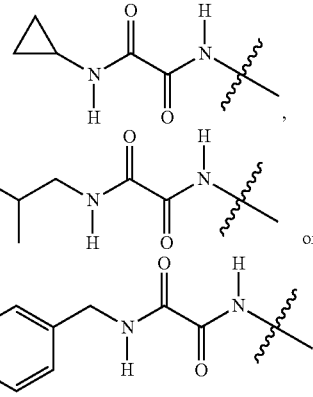

According to another embodiment of compounds of formula I, V is —C(O)— and R is a bond.

According to another embodiment of compounds of formula I, V is —C(O)—, R is a bond, and T is:
(C3-C10)-heterocyclyl- or (C5-C10)heteroaryl-;
  wherein each T is optionally substituted with up to 3 J substituents.
According to another embodiment, T is (C5-C6)heterocyclyl- or (C5-C6)heteroaryl-;
  wherein each T is optionally substituted with up to 3 J substituents.
According to another embodiment, T is:

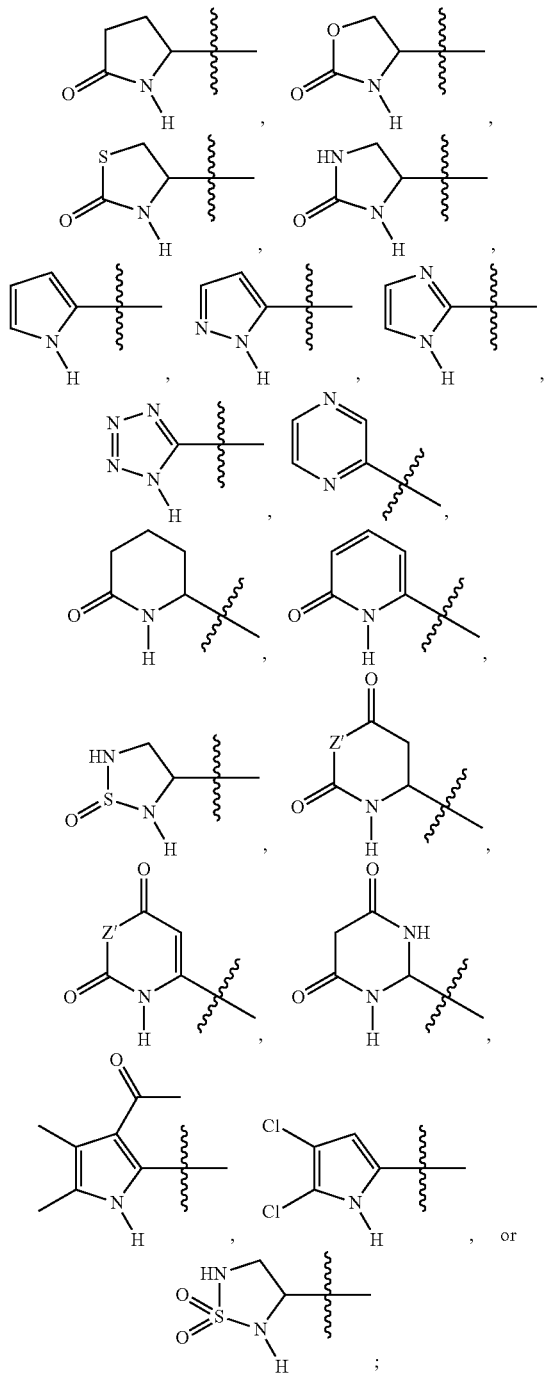

wherein:
  Z' is independently O, S, NR', or C(R')$_2$.

According to another embodiment, T is:

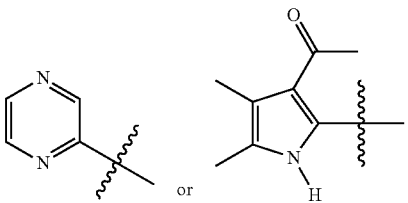

According to another embodiment, this invention does not include the following compounds:
1. 3-Acetyl-4,5-dimethyl-1H-pyrrole-2-carboxylic acid (cyclohexyl-{1-[3-cyclohexyl-2-(1-cyclopropylaminooxalyl-butylcarbamoyl)-pyrrolidine-1-carbonyl]-2,2-dimethyl-propylcarbamoyl}-methyl)-amide;
2. 3-Acetyl-4,5-dimethyl-1H-pyrrole-2-carboxylic acid (cyclohexyl-{1-[2-(1-cyclopropylaminooxalyl-butylcarbamoyl)-3-isopropyl-pyrrolidine-1-carbonyl]-2,2-dimethyl-propylcarbamoyl}-methyl)-amide;
3. 3-Acetyl-4,5-dimethyl-1H-pyrrole-2-carboxylic acid (cyclohexyl-{1-[2-(1-cyclopropylaminooxalyl-butylcarbamoyl)-4-(quinazolin-4-yloxy)-pyrrolidine-1-carbonyl]-2,2-dimethyl-propylcarbamoyl}-methyl)-amide; and
4. 3-Acetyl-4,5-dimethyl-1H-pyrrole-2-carboxylic acid ({1-[4-(5-chloro-pyridin-2-yloxy)-2-(1-cyclopropylaminooxalyl-butylcarbamoyl)-pyrrolidine-1-carbonyl]-2,2-dimethyl-propylcarbamoyl}-cyclohexyl-methyl)-amide (e.g., compounds 63, 64, 66, and 67 of WO 03/087092).

According to yet another embodiment, this invention does not include the following compounds
wherein:
V is —C(O)—, R is a bond, T is the (C5-C10)-heteroaryl 3-acetyl-4,5-dimethyl-1H-pyrrole and
the

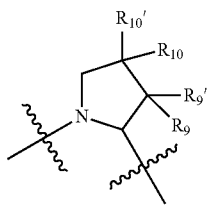

radical is:

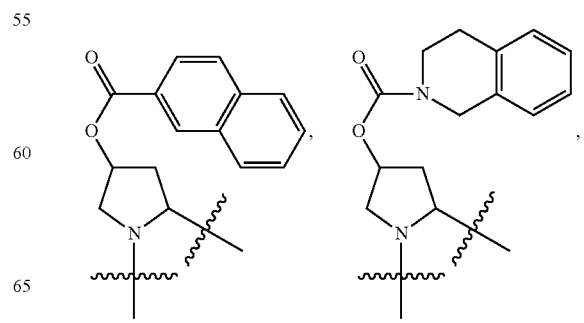

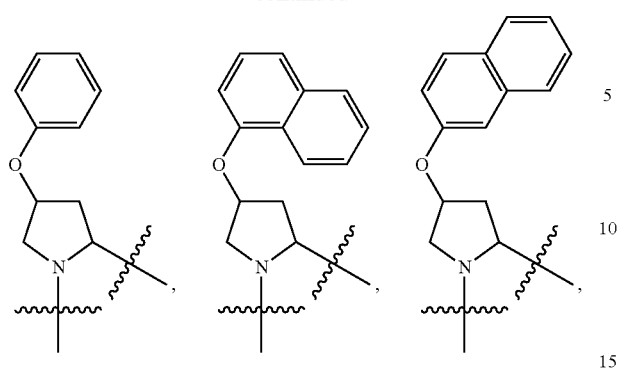
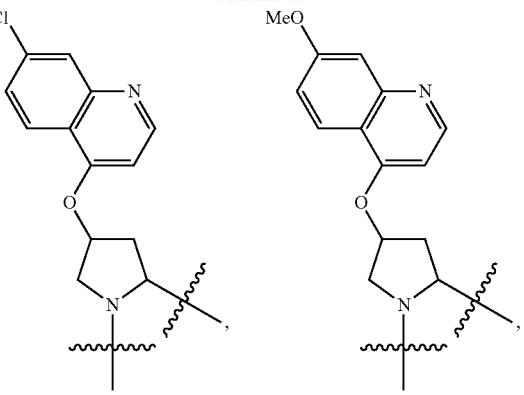
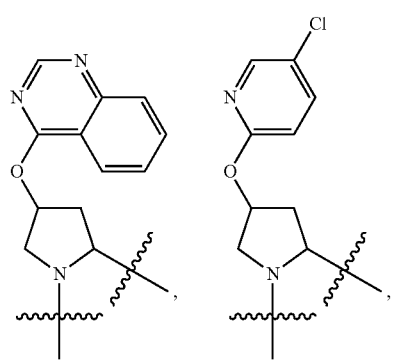
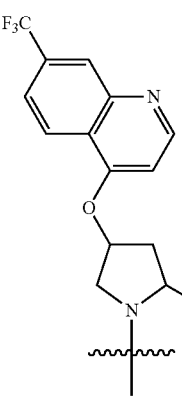
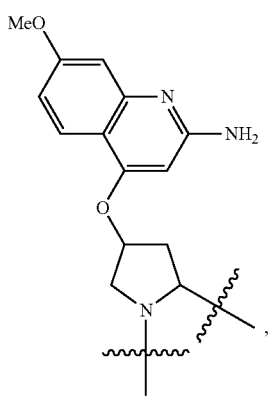
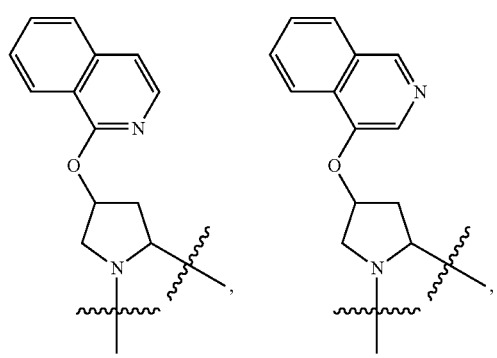
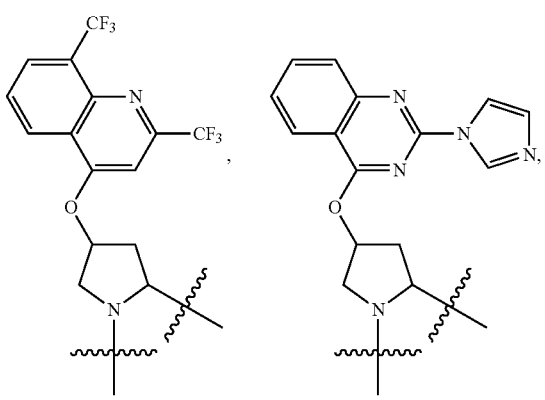
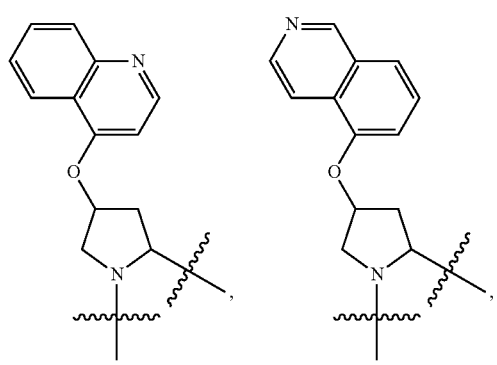
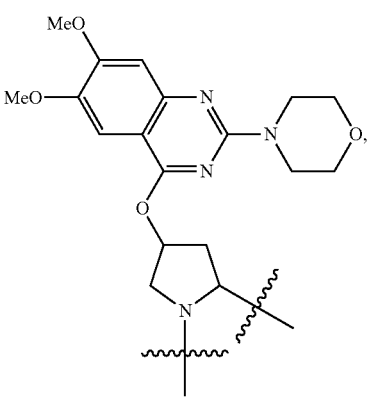

-continued

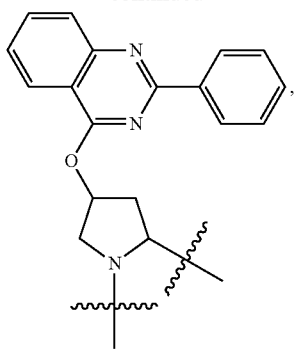,

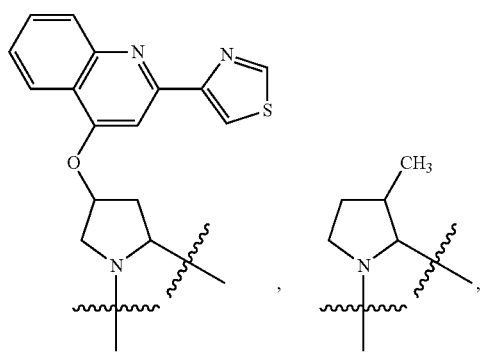,

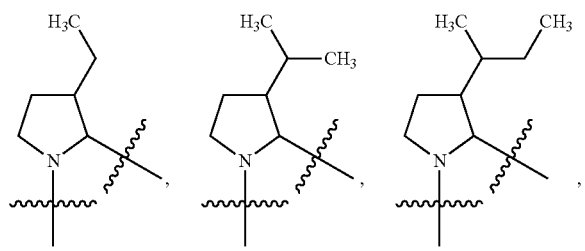,

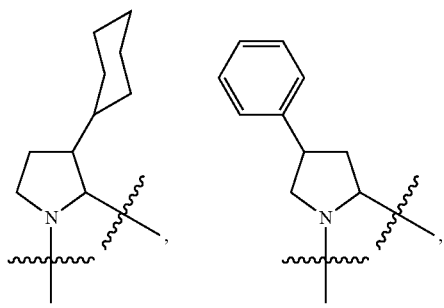,

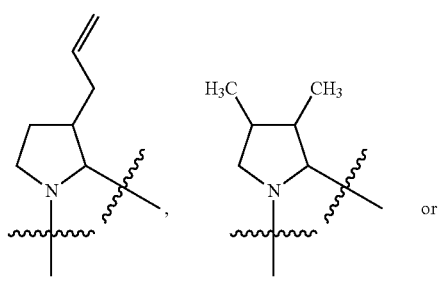 or

-continued

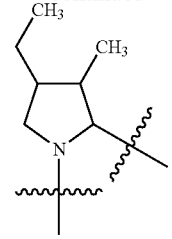

(e.g., substituted proline radicals at pages 56 and 57 of WO 03/087092).

According to another embodiment, this invention does not include compounds wherein:
V is —C(O)—;
R is a bond; and
T is 3-acetyl-4,5-dimethyl-1H-pyrrole (e.g., compounds of formula II" at page 85 of WO 03/087092).

According to another embodiment, this invention does not include compounds wherein T is a C5-heteroaryl (e.g., compounds of formula II at page 22 of WO 03/087092).

According to another embodiment, this invention does not include compounds wherein T is an optionally substituted pyrrole group (e.g., compounds of formula II at page 22 of WO 03/087092).

According to another embodiment, this invention does not include compounds wherein:
V is —C(O)—, —S(O)—, or —S(O)$_2$—:
R is a bond; and
T is:

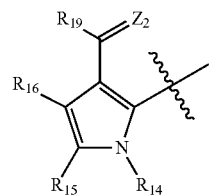

wherein:
$R_{14}$ is —H, —S(O)R', —S(O)$_2$R', —C(O)R', —C(O)OR', —C(O)N(R')$_2$, —N(R')C(O)R', —N(COR')COR', —SO$_2$N(R')$_2$, —SO$_3$R', —C(O)C(O)R', —C(O)CH$_2$C(O)R', —C(S)R', —C(S)N(R')$_4$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_4$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O) (OR')$_2$, or —P(O)(H)(OR');

$R_{15}$ and $R_{16}$ are independently halogen, —OR', —OC(O)N(R')$_2$, —NO$_2$, —CN, —CF$_3$, —OCF$_3$, —R', oxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_4$, —OC(O)N(R')$_2$, —C(S)N(R')$_4$, —(CH$_2$)$_{0-2}$NHC(O)R', —N(R')N(R')COR', —N(R')N(R')C(O)OR', —N(R')N(R')CON(R')$_4$, —N(R') SO$_2$R', —N(R') SO$_2$N(R')$_2$, —N(R') C(O) OR', —N(R') C(O)R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR');

$Z_2$ is =O, =NR', =NOR', or =C(R')$_2$;

$R_{19}$ is —OR', —CF$_3$, —OCF$_3$, —R', —N(R')$_2$, —SR', —C(O)R', —COOR', —CON(R')$_2$, —N(R')COR', or —N(COR')COR'; wherein two R' groups together with the atoms to which they are bound form a 3- to 10-membered aromatic or non-aromatic ring having up to 3 heteroatoms independently selected from N, NH, O, S, SO, or SO$_2$, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from J$_2$; or each R' is independently selected from:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, or
(C5-C10)-heteroaryl-(C1-C12)-aliphatic-,
wherein R' has up to 3 substituents selected independently from J$_2$; and J$_2$ is halogen, —OR', —OC(O)N(R')$_2$, —NO$_2$, —CN, —CF$_3$, —OCF$_3$, —R', oxo, thioxo, 1,2-methylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O) OR', —N(R') C(O) R', —N(R')C(S)R', —N(R')C(O)N(R')$_2$, —N(R')C(S)N(R')$_2$, —N(COR')COR', —N(OR')R', —CN, —C(=NH)N(R')$_2$, —C(O)N(OR')R', —C(=NOR')R', —OP(O)(OR')$_2$, —P(O)(R')$_2$, —P(O) (OR')$_2$, or —P(O)(H)(OR') (e.g., compounds of formula II at page 22 of WO 03/087092).

According to another preferred embodiment in compounds of formula I, the compound is:

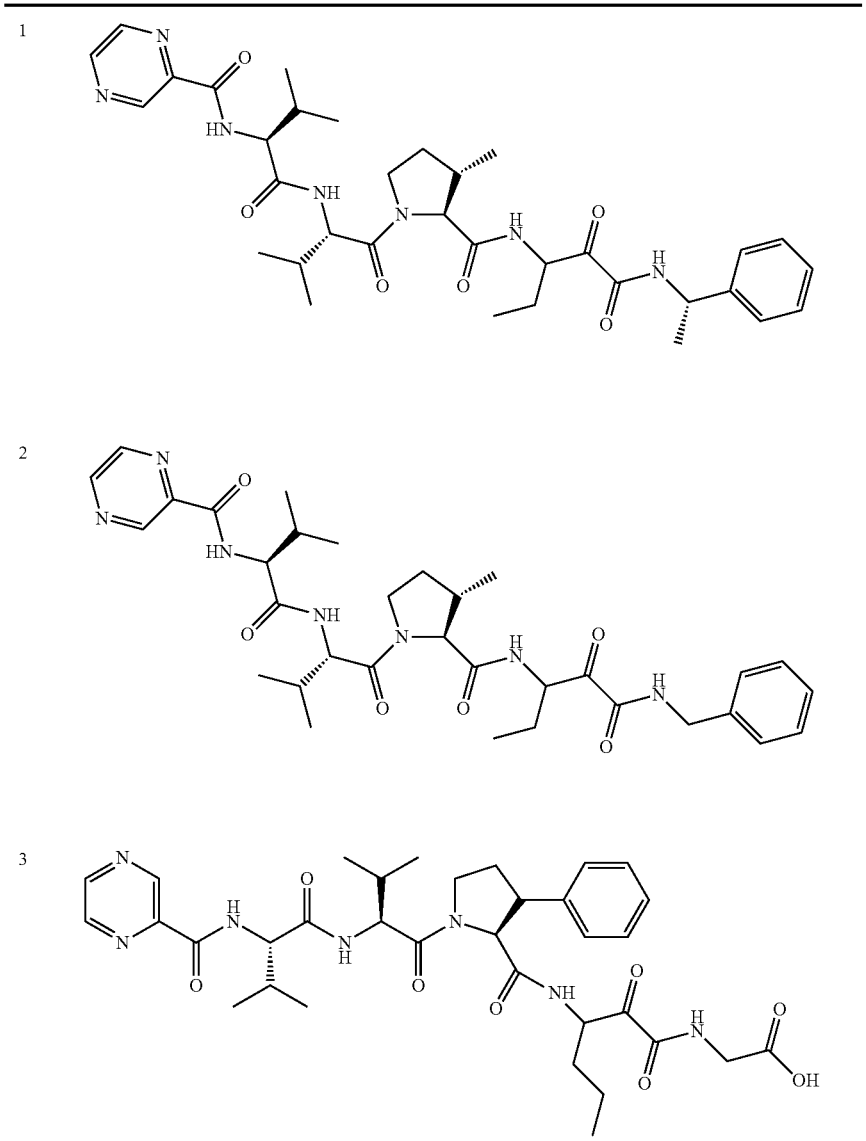

4
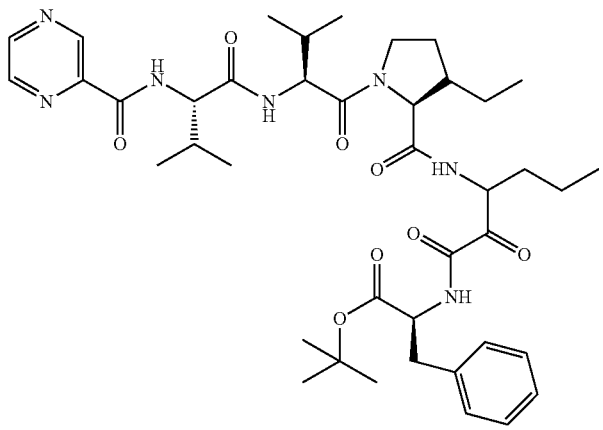
5
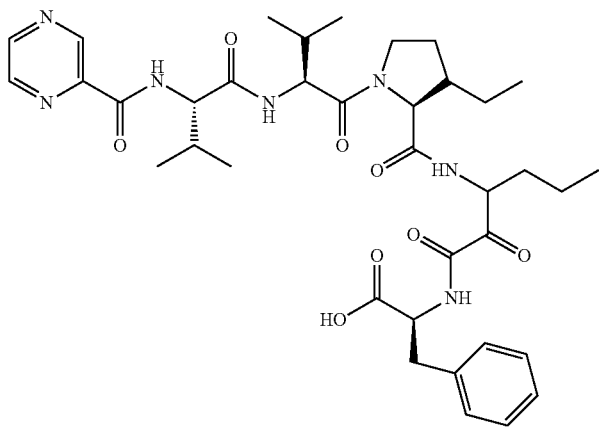
6
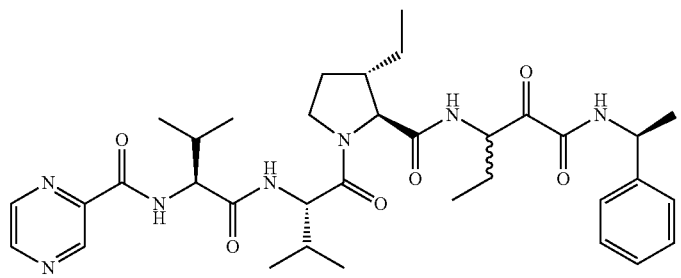 [SMILES: CCC(NC(=O)[C@@H]1[C@@H](CC)CCN1C(=O)[C@@H](NC(=O)[C@@H](NC(=O)c1cnccn1)C(C)C)C(C)C)C(=O)C(=O)N[C@@H](C)c1ccccc1]
7
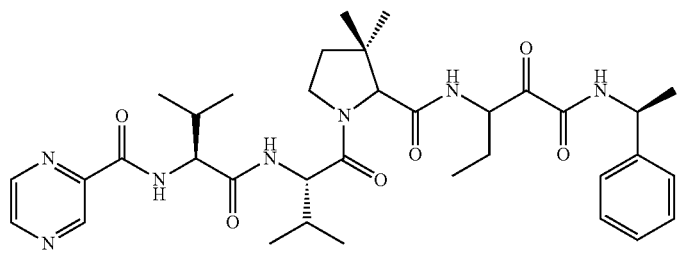

-continued
8
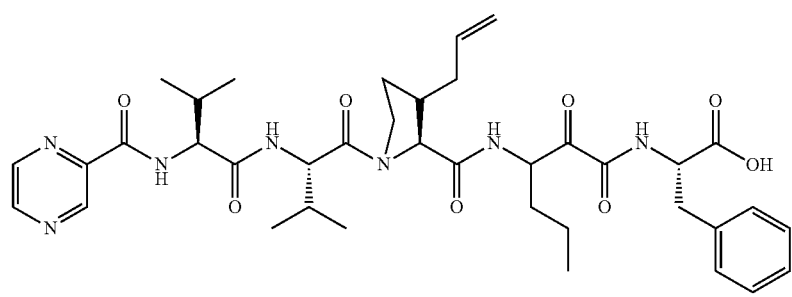
9
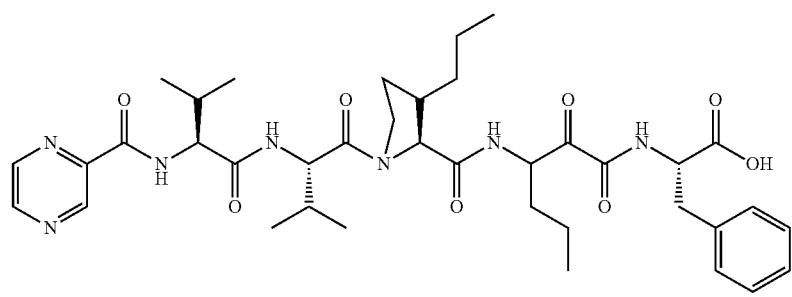
10
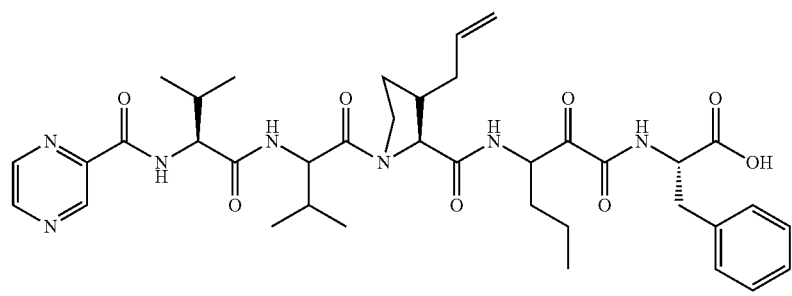
11
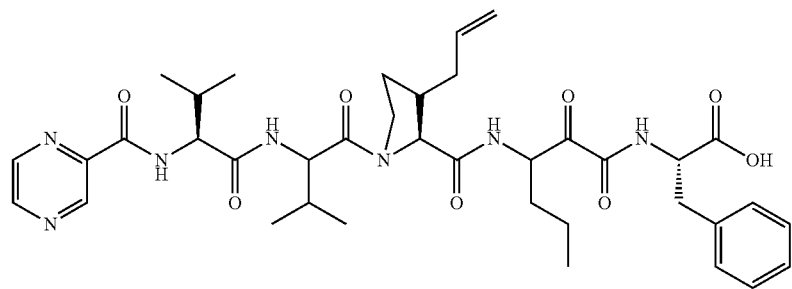
12
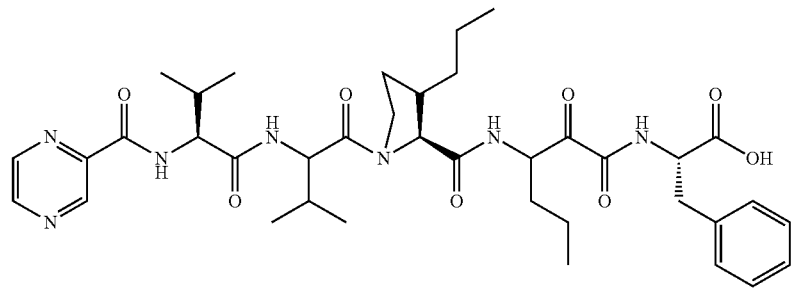

13
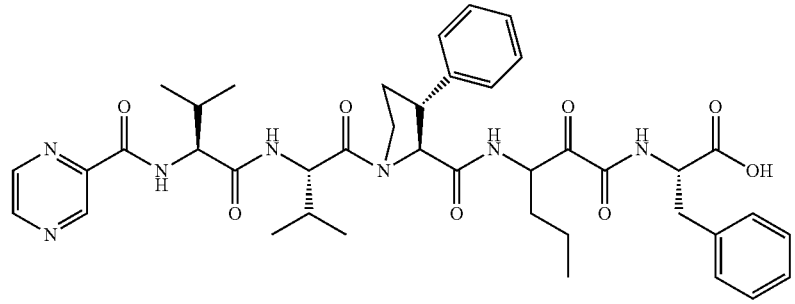
14
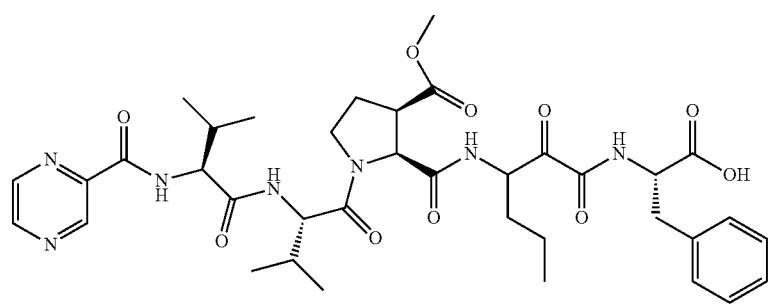 [SMILES: CCCC(NC(=O)[C@@H]1[C@H](C(=O)OC)CCN1C(=O)[C@@H](NC(=O)[C@@H](NC(=O)c1cnccn1)C(C)C)C(C)C)C(=O)C(=O)N[C@@H](Cc1ccccc1)C(=O)O]
15
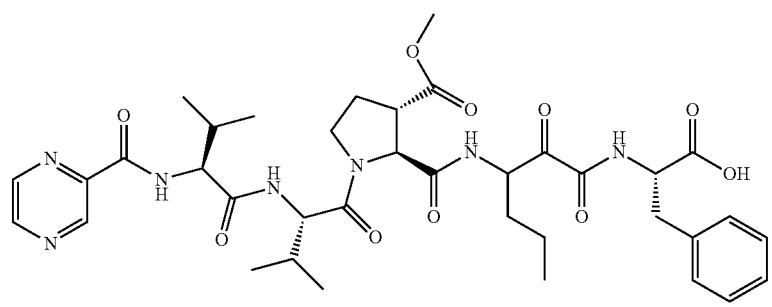 [SMILES: CCCC(NC(=O)[C@@H]1[C@@H](C(=O)OC)CCN1C(=O)[C@@H](NC(=O)[C@@H](NC(=O)c1cnccn1)C(C)C)C(C)C)C(=O)C(=O)N[C@@H](Cc1ccccc1)C(=O)O]
16
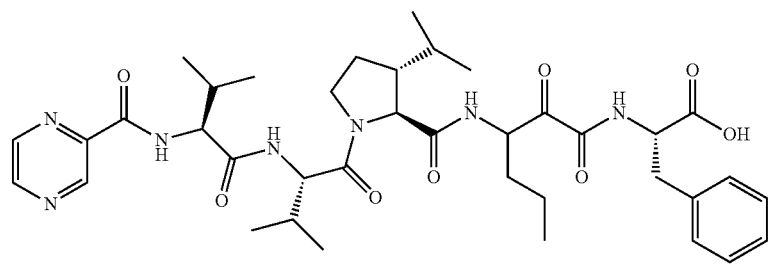 [SMILES: CCCC(NC(=O)[C@@H]1[C@@H](C(C)C)CCN1C(=O)[C@@H](NC(=O)[C@@H](NC(=O)c1cnccn1)C(C)C)C(C)C)C(=O)C(=O)N[C@@H](Cc1ccccc1)C(=O)O]
17
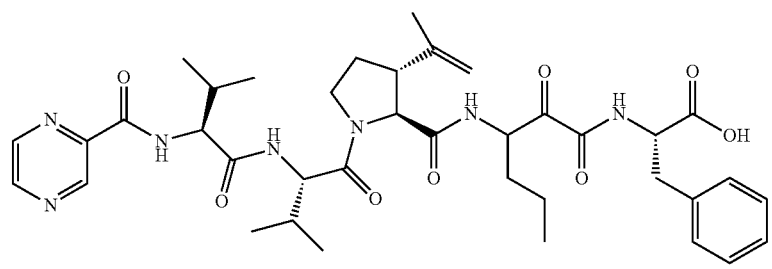 [SMILES: C=C(C)[C@H]1CCN(C(=O)[C@@H](NC(=O)[C@@H](NC(=O)c2cnccn2)C(C)C)C(C)C)[C@@H]1C(=O)NC(CCC)C(=O)C(=O)N[C@@H](Cc1ccccc1)C(=O)O]

-continued
| 18 | 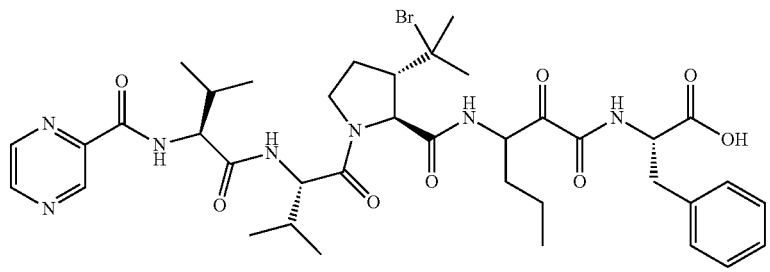 [SMILES: CCCC(NC(=O)[C@@H]1[C@@H](C(C)(C)Br)CCN1C(=O)[C@@H](NC(=O)[C@@H](NC(=O)c1cnccn1)C(C)C)C(C)C)C(=O)C(=O)N[C@@H](Cc1ccccc1)C(=O)O] |
| 19 | 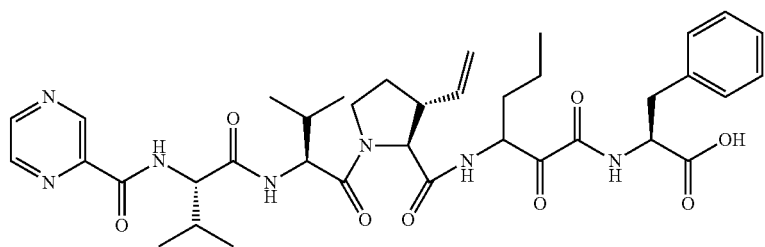 [SMILES: C=C[C@H]1CCN(C(=O)[C@@H](NC(=O)[C@@H](NC(=O)c2cnccn2)C(C)C)C(C)C)[C@@H]1C(=O)NC(CCC)C(=O)C(=O)N[C@@H](Cc1ccccc1)C(=O)O] |
| 20 | 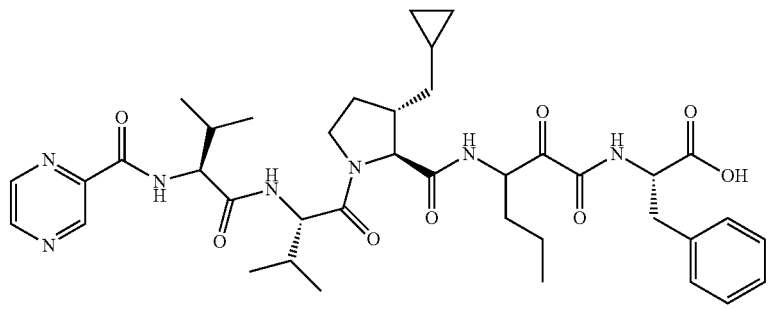 [SMILES: CCCC(NC(=O)[C@@H]1[C@@H](CC2CC2)CCN1C(=O)[C@@H](NC(=O)[C@@H](NC(=O)c1cnccn1)C(C)C)C(C)C)C(=O)C(=O)N[C@@H](Cc1ccccc1)C(=O)O] |
| 21 | 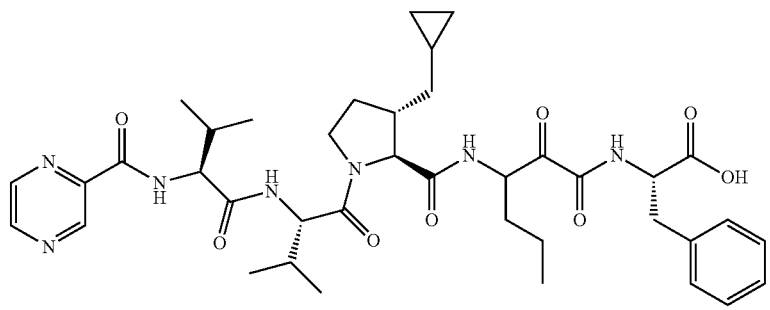 [SMILES: CCCC(NC(=O)[C@@H]1[C@@H](CC2CC2)CCN1C(=O)[C@@H](NC(=O)[C@@H](NC(=O)c1cnccn1)C(C)C)C(C)C)C(=O)C(=O)N[C@@H](Cc1ccccc1)C(=O)O] |
| 22 | 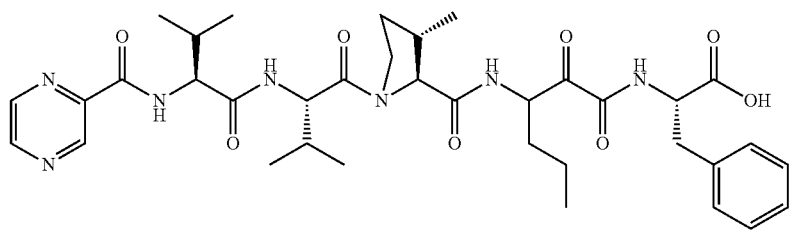 |
| 23 | 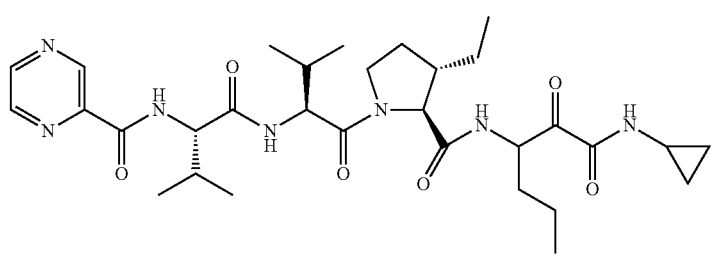 [SMILES: CCCC(NC(=O)[C@@H]1[C@@H](CC)CCN1C(=O)[C@@H](NC(=O)[C@@H](NC(=O)c1cnccn1)C(C)C)C(C)C)C(=O)C(=O)NC1CC1] |

24
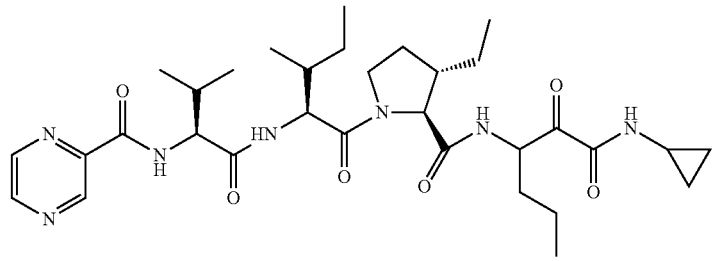 [SMILES: CCCC(NC(=O)[C@@H]1[C@@H](CC)CCN1C(=O)[C@@H](NC(=O)[C@@H](NC(=O)c1cnccn1)C(C)C)C(C)CC)C(=O)C(=O)NC1CC1]
25
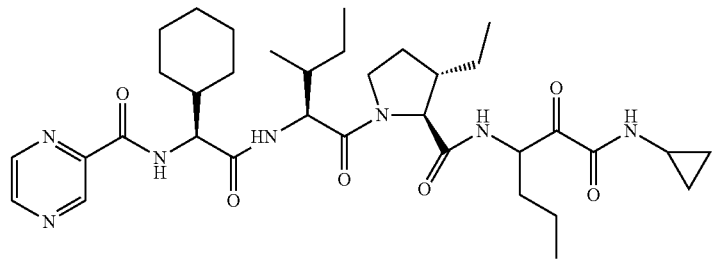 [SMILES: CCCC(NC(=O)[C@@H]1[C@@H](CC)CCN1C(=O)[C@@H](NC(=O)[C@@H](NC(=O)c1cnccn1)C1CCCCC1)C(C)CC)C(=O)C(=O)NC1CC1]
26
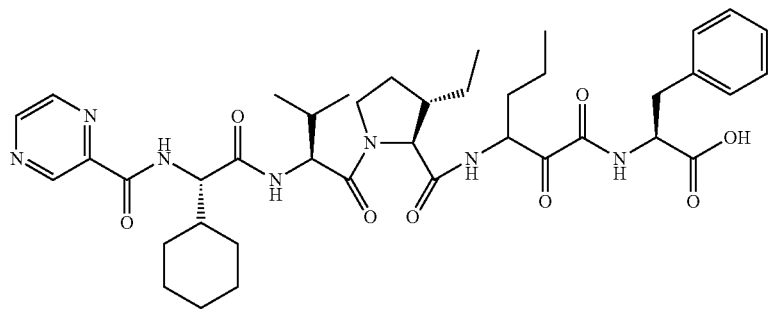 [SMILES: CCCC(NC(=O)[C@@H]1[C@@H](CC)CCN1C(=O)[C@@H](NC(=O)[C@@H](NC(=O)c1cnccn1)C1CCCCC1)C(C)C)C(=O)C(=O)N[C@@H](Cc1ccccc1)C(=O)O]
27
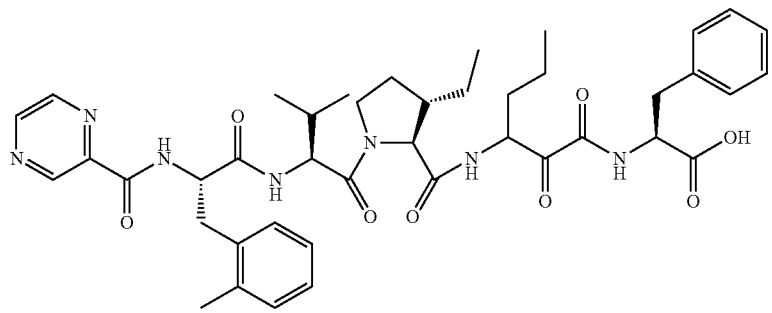 [SMILES: CCCC(NC(=O)[C@@H]1[C@@H](CC)CCN1C(=O)[C@@H](NC(=O)[C@H](Cc1ccccc1C)NC(=O)c1cnccn1)C(C)C)C(=O)C(=O)N[C@@H](Cc1ccccc1)C(=O)O]
28
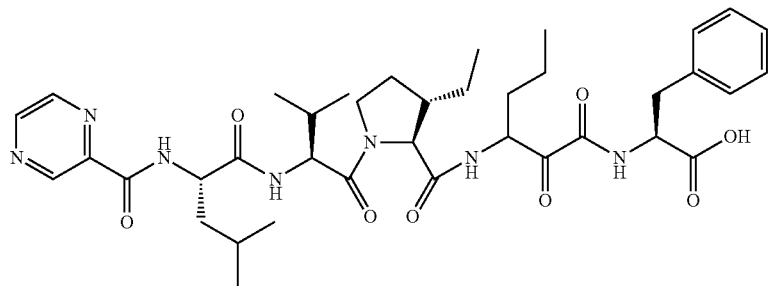 [SMILES: CCCC(NC(=O)[C@@H]1[C@@H](CC)CCN1C(=O)[C@@H](NC(=O)[C@H](CC(C)C)NC(=O)c1cnccn1)C(C)C)C(=O)C(=O)N[C@@H](Cc1ccccc1)C(=O)O]

-continued
29
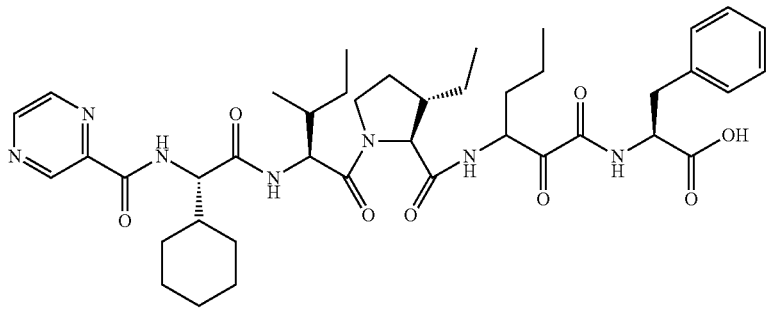 [SMILES: CCCC(NC(=O)[C@@H]1[C@@H](CC)CCN1C(=O)[C@@H](NC(=O)[C@@H](NC(=O)c1cnccn1)C1CCCCC1)C(C)CC)C(=O)C(=O)N[C@@H](Cc1ccccc1)C(=O)O]
30
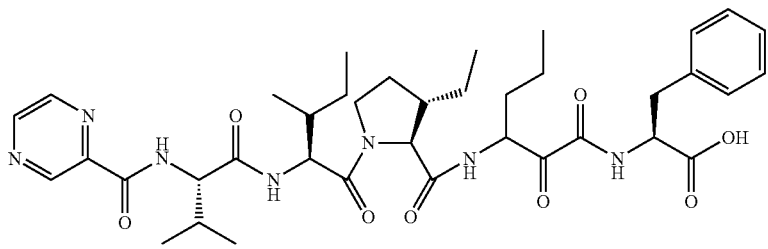 [SMILES: CCCC(NC(=O)[C@@H]1[C@@H](CC)CCN1C(=O)[C@@H](NC(=O)[C@@H](NC(=O)c1cnccn1)C(C)C)C(C)CC)C(=O)C(=O)N[C@@H](Cc1ccccc1)C(=O)O]
31
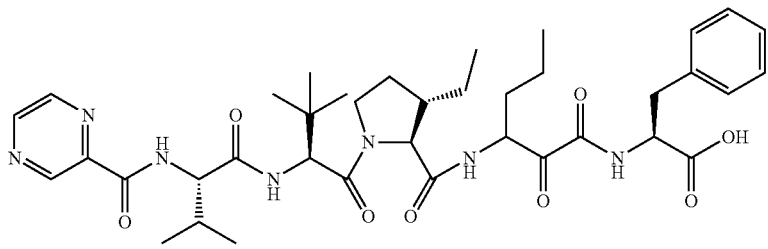 [SMILES: CCCC(NC(=O)[C@@H]1[C@@H](CC)CCN1C(=O)[C@@H](NC(=O)[C@@H](NC(=O)c1cnccn1)C(C)C)C(C)(C)C)C(=O)C(=O)N[C@@H](Cc1ccccc1)C(=O)O]
32
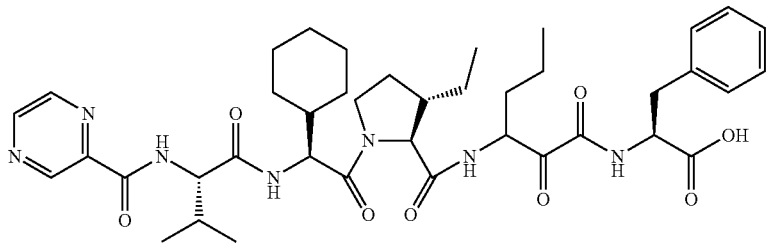 [SMILES: CCCC(NC(=O)[C@@H]1[C@@H](CC)CCN1C(=O)[C@@H](NC(=O)[C@@H](NC(=O)c1cnccn1)C(C)C)C1CCCCC1)C(=O)C(=O)N[C@@H](Cc1ccccc1)C(=O)O]
33
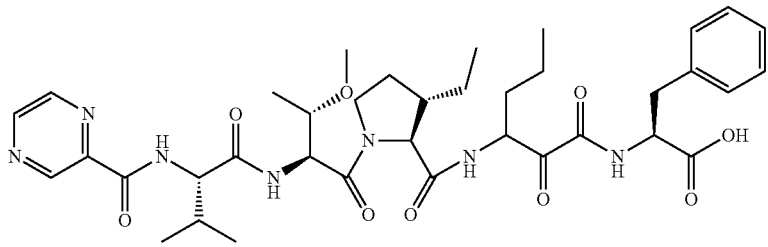 [SMILES: CCCC(NC(=O)[C@@H]1[C@@H](CC)CCN1C(=O)[C@@H](NC(=O)[C@@H](NC(=O)c1cnccn1)C(C)C)[C@H](C)OC)C(=O)C(=O)N[C@@H](Cc1ccccc1)C(=O)O]
34
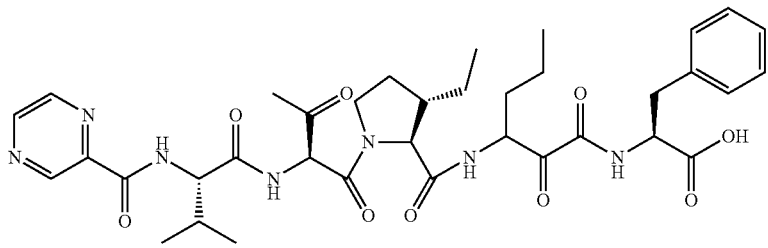 [SMILES: CCCC(NC(=O)[C@@H]1[C@@H](CC)CCN1C(=O)[C@@H](NC(=O)[C@@H](NC(=O)c1cnccn1)C(C)C)C(C)=O)C(=O)C(=O)N[C@@H](Cc1ccccc1)C(=O)O]

35 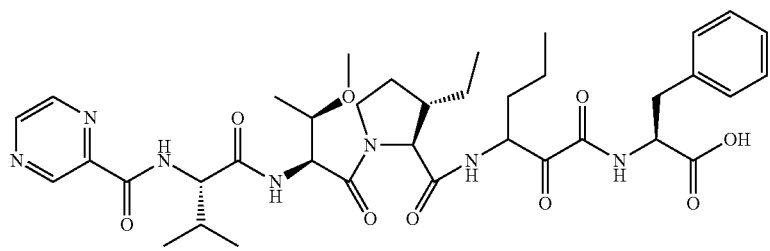 [SMILES: CCCC(NC(=O)[C@@H]1[C@@H](CC)CCN1C(=O)[C@@H](NC(=O)[C@@H](NC(=O)c1cnccn1)C(C)C)[C@@H](C)OC)C(=O)C(=O)N[C@@H](Cc1ccccc1)C(=O)O]
36 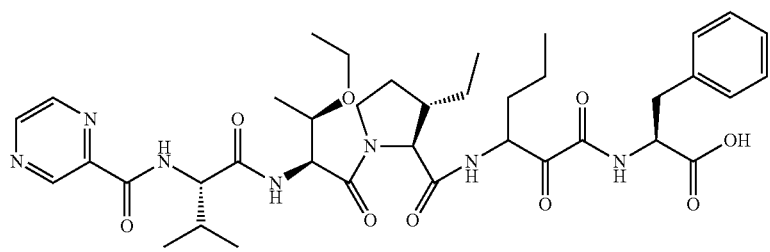 [SMILES: CCCC(NC(=O)[C@@H]1[C@@H](CC)CCN1C(=O)[C@@H](NC(=O)[C@@H](NC(=O)c1cnccn1)C(C)C)[C@@H](C)OCC)C(=O)C(=O)N[C@@H](Cc1ccccc1)C(=O)O]
37 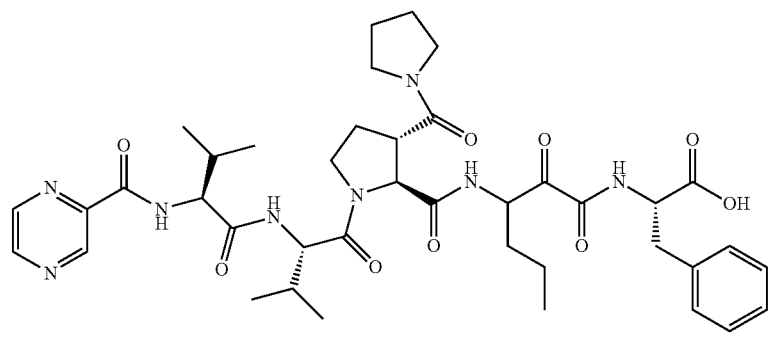 [SMILES: CCCC(NC(=O)[C@@H]1[C@@H](C(=O)N2CCCC2)CCN1C(=O)[C@@H](NC(=O)[C@@H](NC(=O)c1cnccn1)C(C)C)C(C)C)C(=O)C(=O)N[C@@H](Cc1ccccc1)C(=O)O]
38 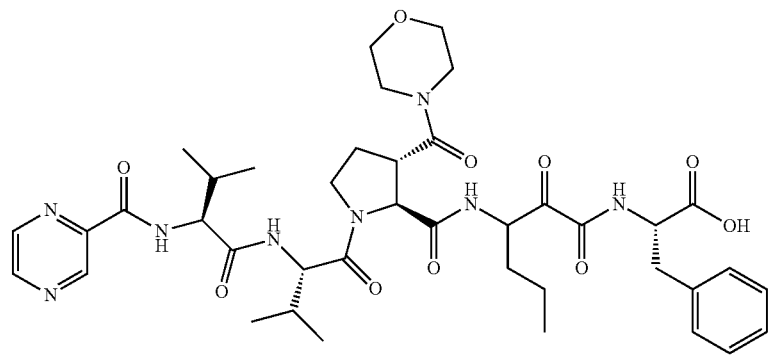 [SMILES: CCCC(NC(=O)[C@@H]1[C@@H](C(=O)N2CCOCC2)CCN1C(=O)[C@@H](NC(=O)[C@@H](NC(=O)c1cnccn1)C(C)C)C(C)C)C(=O)C(=O)N[C@@H](Cc1ccccc1)C(=O)O]
39 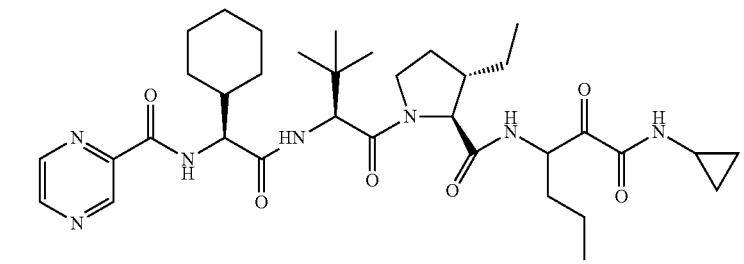 [SMILES: CCCC(NC(=O)[C@@H]1[C@@H](CC)CCN1C(=O)[C@@H](NC(=O)[C@@H](NC(=O)c1cnccn1)C1CCCCC1)C(C)(C)C)C(=O)C(=O)NC1CC1]

40 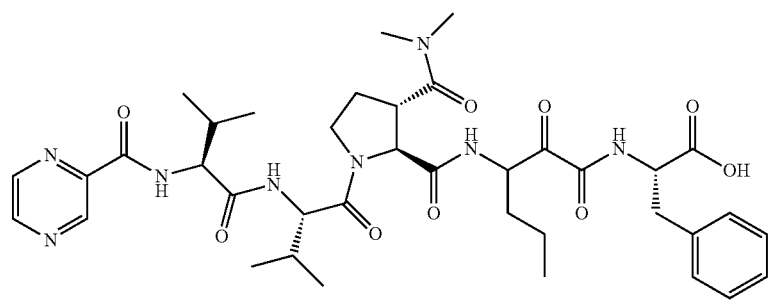 [SMILES: CCCC(NC(=O)[C@@H]1[C@@H](C(=O)N(C)C)CCN1C(=O)[C@@H](NC(=O)[C@@H](NC(=O)c1cnccn1)C(C)C)C(C)C)C(=O)C(=O)N[C@@H](Cc1ccccc1)C(=O)O]
41 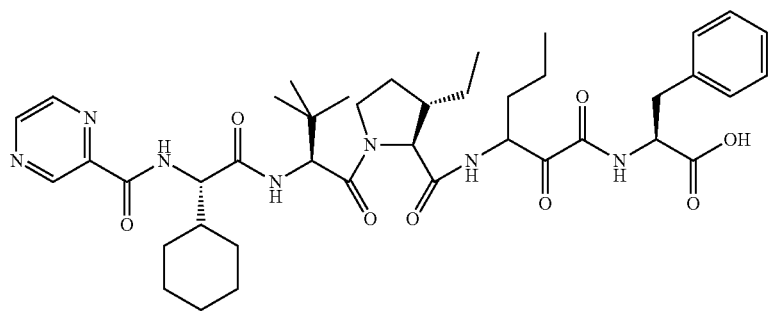 [SMILES: CCCC(NC(=O)[C@@H]1[C@@H](CC)CCN1C(=O)[C@@H](NC(=O)[C@@H](NC(=O)c1cnccn1)C1CCCCC1)C(C)(C)C)C(=O)C(=O)N[C@@H](Cc1ccccc1)C(=O)O]
42 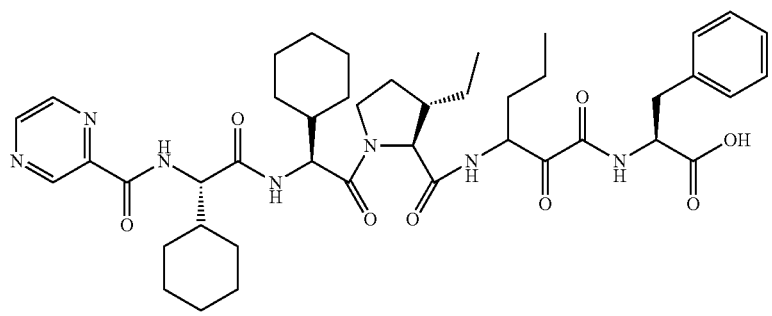 [SMILES: CCCC(NC(=O)[C@@H]1[C@@H](CC)CCN1C(=O)[C@@H](NC(=O)[C@@H](NC(=O)c1cnccn1)C1CCCCC1)C1CCCCC1)C(=O)C(=O)N[C@@H](Cc1ccccc1)C(=O)O]
43 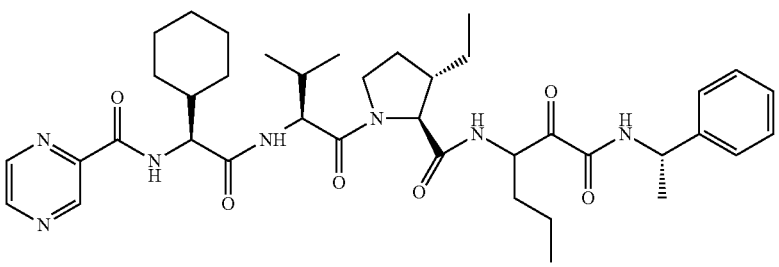 [SMILES: CCCC(NC(=O)[C@@H]1[C@@H](CC)CCN1C(=O)[C@@H](NC(=O)[C@@H](NC(=O)c1cnccn1)C1CCCCC1)C(C)C)C(=O)C(=O)N[C@@H](C)c1ccccc1]
44 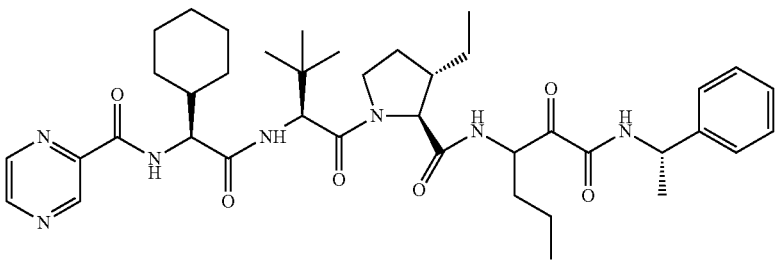 [SMILES: CCCC(NC(=O)[C@@H]1[C@@H](CC)CCN1C(=O)[C@@H](NC(=O)[C@@H](NC(=O)c1cnccn1)C1CCCCC1)C(C)(C)C)C(=O)C(=O)N[C@@H](C)c1ccccc1]

45 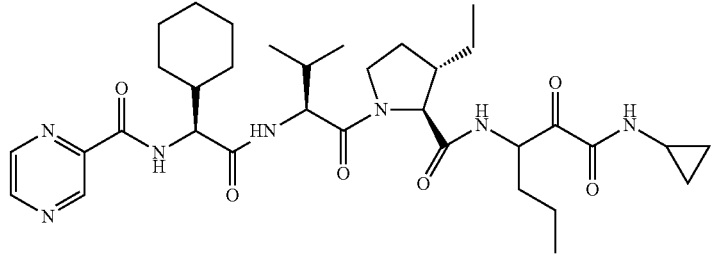 [SMILES: CCCC(NC(=O)[C@@H]1[C@@H](CC)CCN1C(=O)[C@@H](NC(=O)[C@@H](NC(=O)c1cnccn1)C1CCCCC1)C(C)C)C(=O)C(=O)NC1CC1]
46 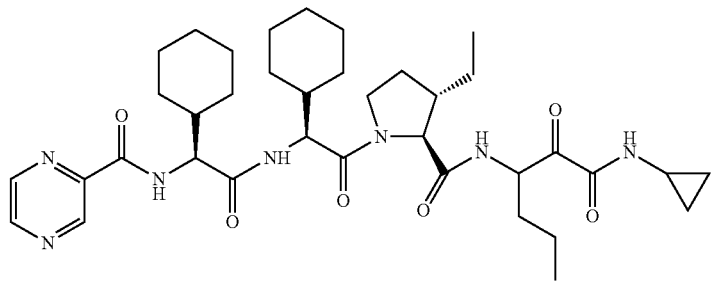 [SMILES: CCCC(NC(=O)[C@@H]1[C@@H](CC)CCN1C(=O)[C@@H](NC(=O)[C@@H](NC(=O)c1cnccn1)C1CCCCC1)C1CCCCC1)C(=O)C(=O)NC1CC1]
47 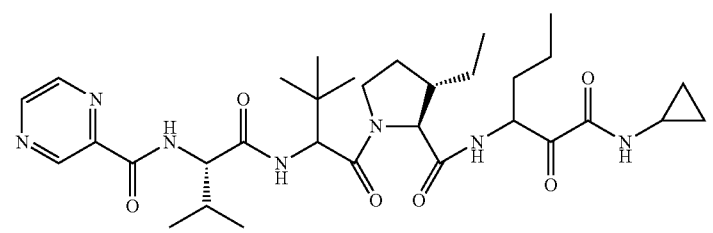 [SMILES: CCCC(NC(=O)[C@@H]1[C@@H](CC)CCN1C(=O)C(NC(=O)[C@@H](NC(=O)c1cnccn1)C(C)C)C(C)(C)C)C(=O)C(=O)NC1CC1]
48 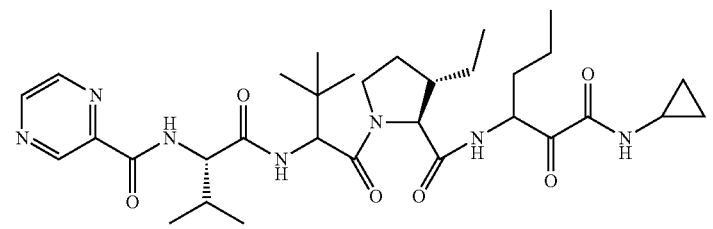 [SMILES: CCCC(NC(=O)[C@@H]1[C@@H](CC)CCN1C(=O)C(NC(=O)[C@@H](NC(=O)c1cnccn1)C(C)C)C(C)(C)C)C(=O)C(=O)NC1CC1]
49 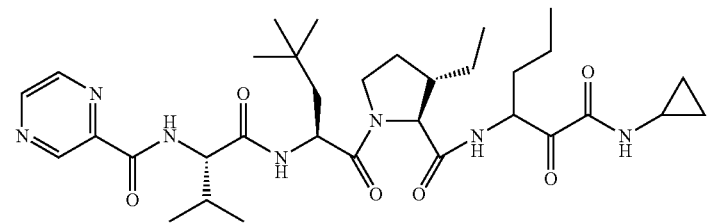 [SMILES: CCCC(NC(=O)[C@@H]1[C@@H](CC)CCN1C(=O)[C@H](CC(C)(C)C)NC(=O)[C@@H](NC(=O)c1cnccn1)C(C)C)C(=O)C(=O)NC1CC1]
50 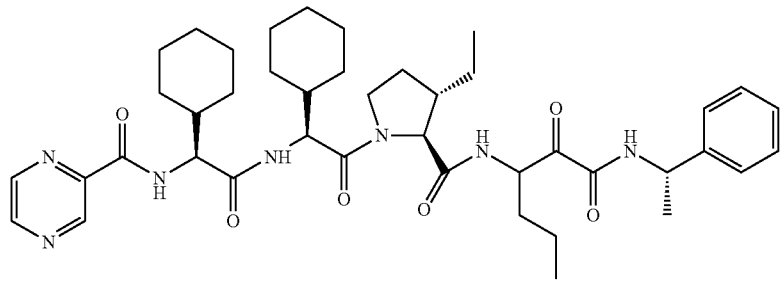 [SMILES: CCCC(NC(=O)[C@@H]1[C@@H](CC)CCN1C(=O)[C@@H](NC(=O)[C@@H](NC(=O)c1cnccn1)C1CCCCC1)C1CCCCC1)C(=O)C(=O)N[C@@H](C)c1ccccc1]

51 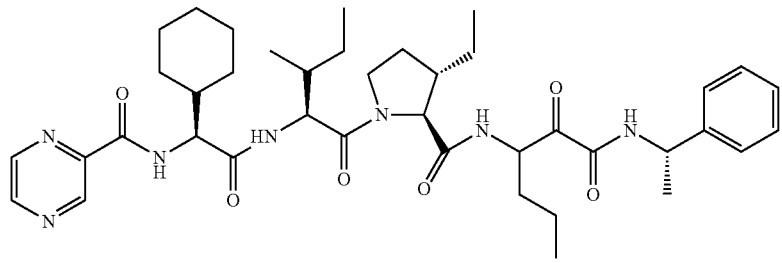 [SMILES: CCCC(NC(=O)[C@@H]1[C@@H](CC)CCN1C(=O)[C@@H](NC(=O)[C@@H](NC(=O)c1cnccn1)C1CCCCC1)C(C)CC)C(=O)C(=O)N[C@@H](C)c1ccccc1]
52 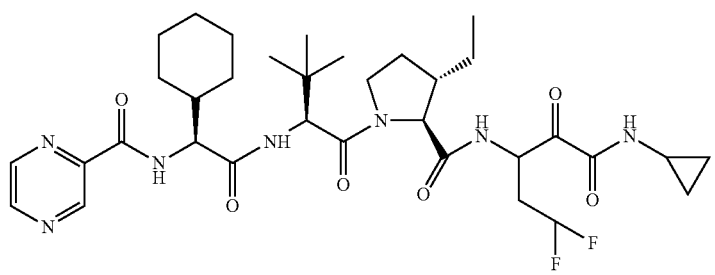 [SMILES: CC[C@H]1CCN(C(=O)[C@@H](NC(=O)[C@@H](NC(=O)c2cnccn2)C2CCCCC2)C(C)(C)C)[C@@H]1C(=O)NC(CC(F)F)C(=O)C(=O)NC1CC1]
53 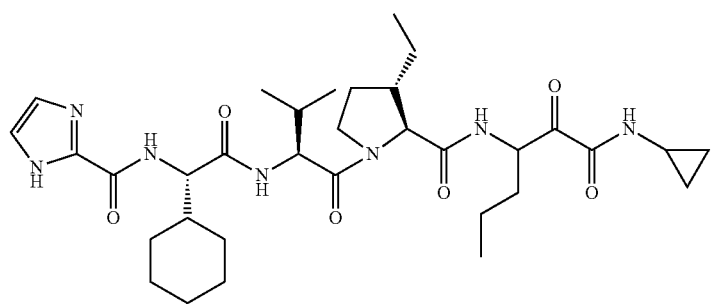 [SMILES: CCCC(NC(=O)[C@@H]1[C@@H](CC)CCN1C(=O)[C@@H](NC(=O)[C@@H](NC(=O)c1ncc[nH]1)C1CCCCC1)C(C)C)C(=O)C(=O)NC1CC1]
54 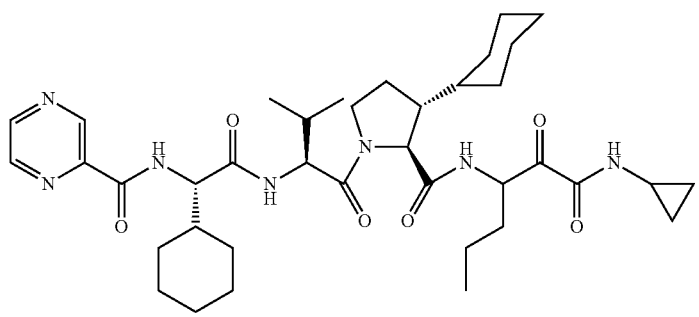 [SMILES: CCCC(NC(=O)[C@@H]1[C@@H](C2CCCCC2)CCN1C(=O)[C@@H](NC(=O)[C@@H](NC(=O)c1cnccn1)C1CCCCC1)C(C)C)C(=O)C(=O)NC1CC1]
55 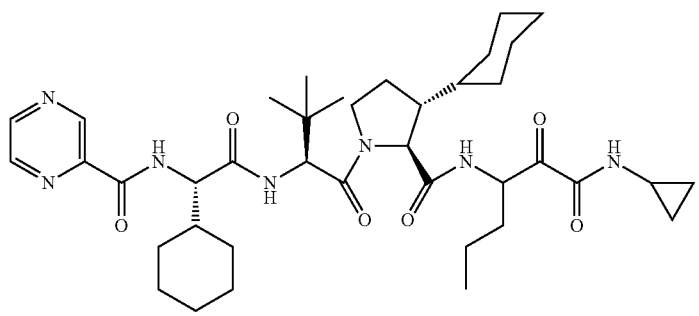 [SMILES: CCCC(NC(=O)[C@@H]1[C@@H](C2CCCCC2)CCN1C(=O)[C@@H](NC(=O)[C@@H](NC(=O)c1cnccn1)C1CCCCC1)C(C)(C)C)C(=O)C(=O)NC1CC1]

56 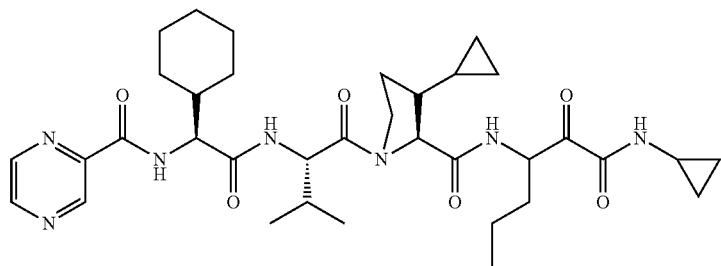
57 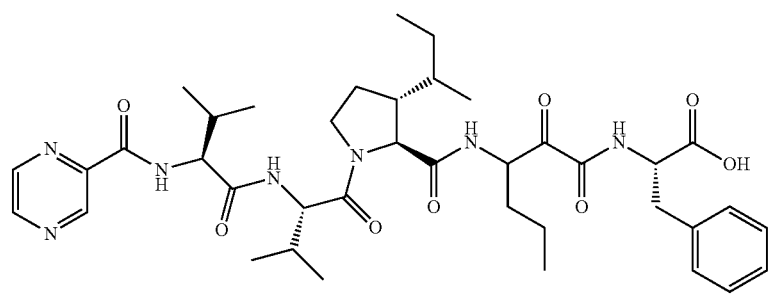 [SMILES: CCCC(NC(=O)[C@@H]1[C@@H](C(C)CC)CCN1C(=O)[C@@H](NC(=O)[C@@H](NC(=O)c1cnccn1)C(C)C)C(C)C)C(=O)C(=O)N[C@@H](Cc1ccccc1)C(=O)O]
58 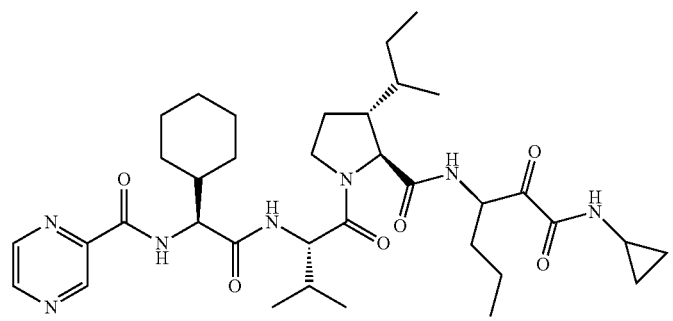 [SMILES: CCCC(NC(=O)[C@@H]1[C@@H](C(C)CC)CCN1C(=O)[C@@H](NC(=O)[C@@H](NC(=O)c1cnccn1)C1CCCCC1)C(C)C)C(=O)C(=O)NC1CC1]
59 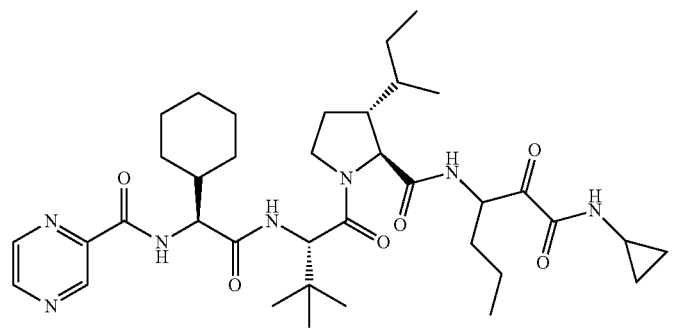 [SMILES: CCCC(NC(=O)[C@@H]1[C@@H](C(C)CC)CCN1C(=O)[C@@H](NC(=O)[C@@H](NC(=O)c1cnccn1)C1CCCCC1)C(C)(C)C)C(=O)C(=O)NC1CC1]
60 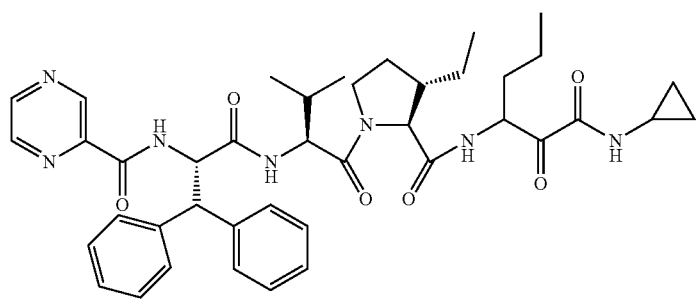 [SMILES: CCCC(NC(=O)[C@@H]1[C@@H](CC)CCN1C(=O)[C@@H](NC(=O)[C@@H](NC(=O)c1cnccn1)C(c1ccccc1)c1ccccc1)C(C)C)C(=O)C(=O)NC1CC1]

61
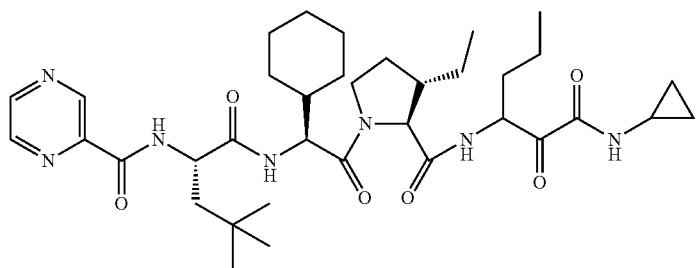 [SMILES: CCCC(NC(=O)[C@@H]1[C@@H](CC)CCN1C(=O)[C@@H](NC(=O)[C@H](CC(C)(C)C)NC(=O)c1cnccn1)C1CCCCC1)C(=O)C(=O)NC1CC1]
62
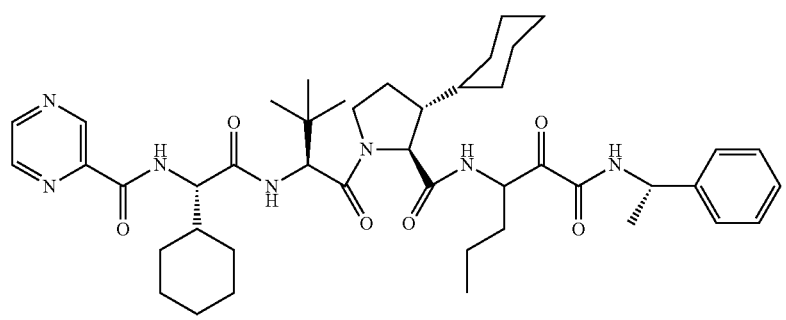 [SMILES: CCCC(NC(=O)[C@@H]1[C@@H](C2CCCCC2)CCN1C(=O)[C@@H](NC(=O)[C@@H](NC(=O)c1cnccn1)C1CCCCC1)C(C)(C)C)C(=O)C(=O)N[C@@H](C)c1ccccc1]
63
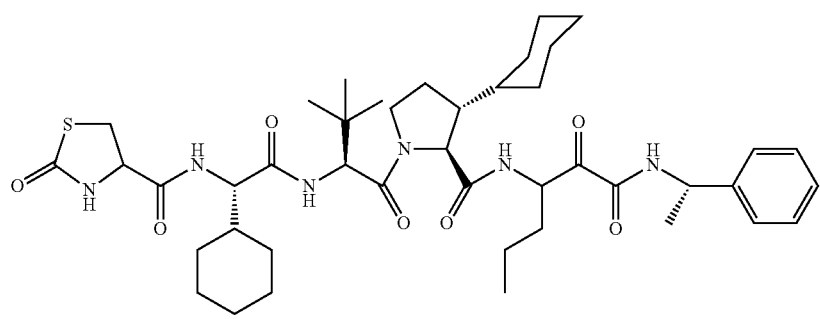 [SMILES: CCCC(NC(=O)[C@@H]1[C@@H](C2CCCCC2)CCN1C(=O)[C@@H](NC(=O)[C@@H](NC(=O)C1CSC(=O)N1)C1CCCCC1)C(C)(C)C)C(=O)C(=O)N[C@@H](C)c1ccccc1]
64
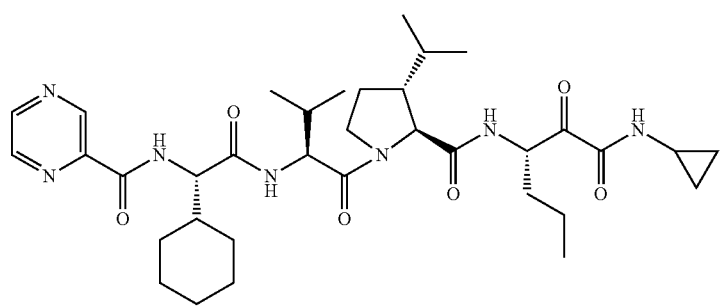 [SMILES: CCC[C@H](NC(=O)[C@@H]1[C@@H](C(C)C)CCN1C(=O)[C@@H](NC(=O)[C@@H](NC(=O)c1cnccn1)C1CCCCC1)C(C)C)C(=O)C(=O)NC1CC1]
65
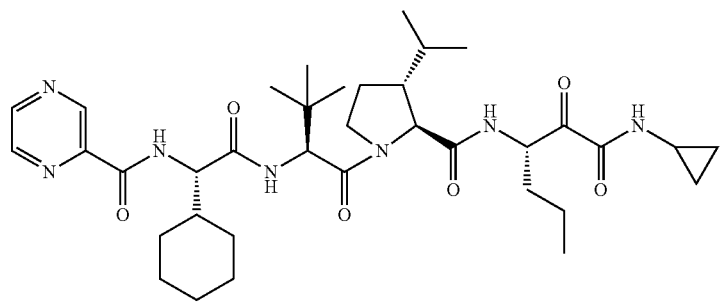 [SMILES: CCC[C@H](NC(=O)[C@@H]1[C@@H](C(C)C)CCN1C(=O)[C@@H](NC(=O)[C@@H](NC(=O)c1cnccn1)C1CCCCC1)C(C)(C)C)C(=O)C(=O)NC1CC1]

66 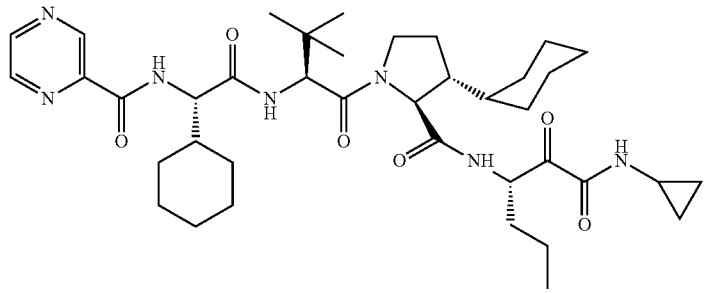 [SMILES: CCC[C@H](NC(=O)[C@@H]1[C@@H](C2CCCCC2)CCN1C(=O)[C@@H](NC(=O)[C@@H](NC(=O)c1cnccn1)C1CCCCC1)C(C)(C)C)C(=O)C(=O)NC1CC1]
67 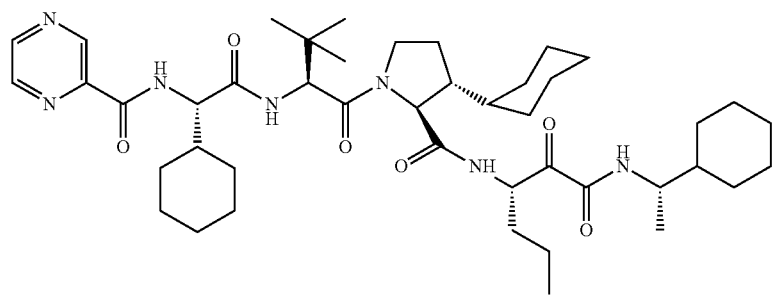 [SMILES: CCC[C@H](NC(=O)[C@@H]1[C@@H](C2CCCCC2)CCN1C(=O)[C@@H](NC(=O)[C@@H](NC(=O)c1cnccn1)C1CCCCC1)C(C)(C)C)C(=O)C(=O)N[C@@H](C)C1CCCCC1]
68 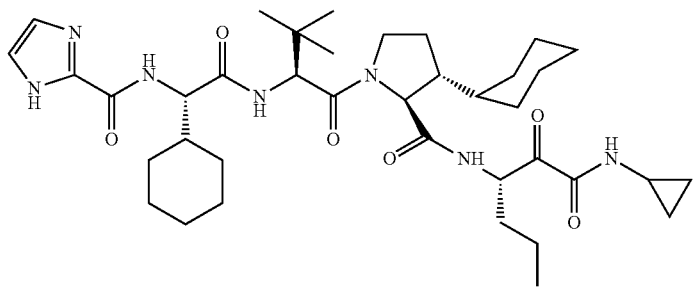 [SMILES: CCC[C@H](NC(=O)[C@@H]1[C@@H](C2CCCCC2)CCN1C(=O)[C@@H](NC(=O)[C@@H](NC(=O)c1ncc[nH]1)C1CCCCC1)C(C)(C)C)C(=O)C(=O)NC1CC1]
69 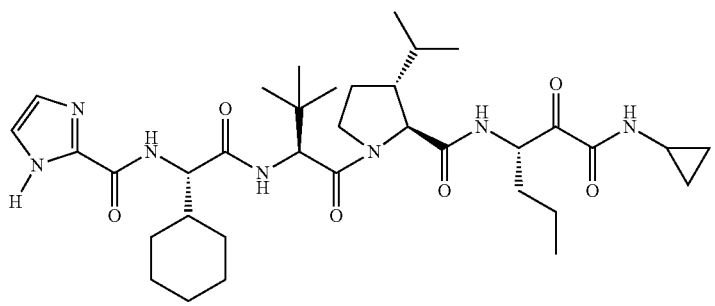 [SMILES: CCC[C@H](NC(=O)[C@@H]1[C@@H](C(C)C)CCN1C(=O)[C@@H](NC(=O)[C@@H](NC(=O)c1ncc[nH]1)C1CCCCC1)C(C)(C)C)C(=O)C(=O)NC1CC1]
70 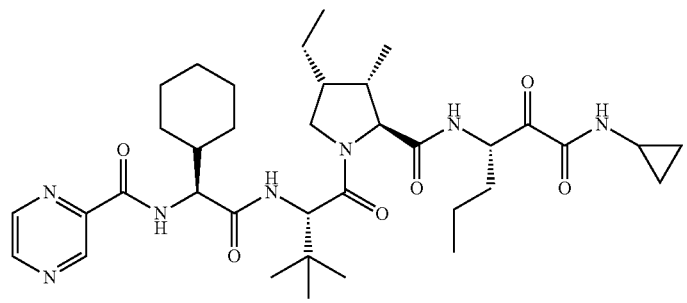

-continued
71
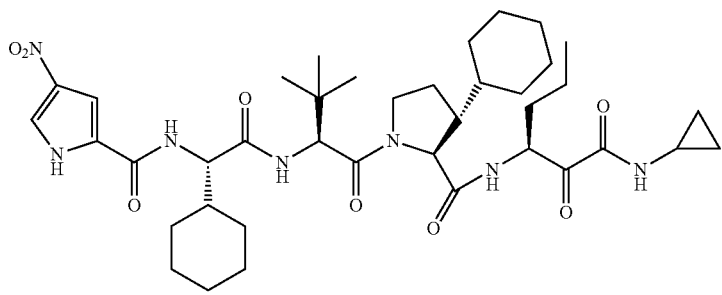 [SMILES: CCC[C@H](NC(=O)[C@@H]1[C@@H](C2CCCCC2)CCN1C(=O)[C@@H](NC(=O)[C@@H](NC(=O)c1cc([N+](=O)[O-])c[nH]1)C1CCCCC1)C(C)(C)C)C(=O)C(=O)NC1CC1]
72
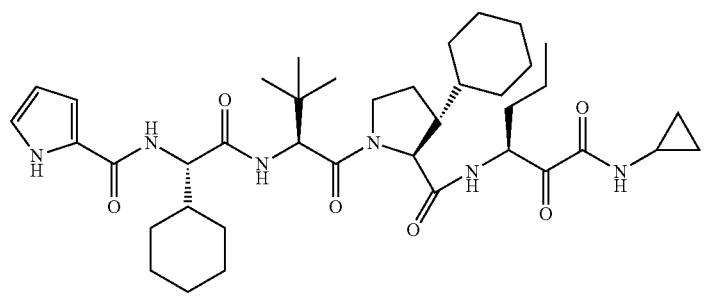 [SMILES: CCC[C@H](NC(=O)[C@@H]1[C@@H](C2CCCCC2)CCN1C(=O)[C@@H](NC(=O)[C@@H](NC(=O)c1ccc[nH]1)C1CCCCC1)C(C)(C)C)C(=O)C(=O)NC1CC1]
73
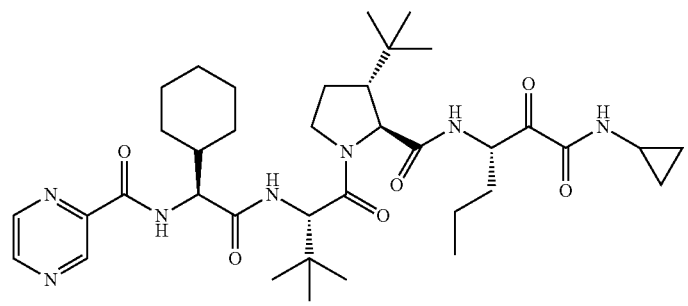 [SMILES: CCC[C@H](NC(=O)[C@@H]1[C@@H](C(C)(C)C)CCN1C(=O)[C@@H](NC(=O)[C@@H](NC(=O)c1cnccn1)C1CCCCC1)C(C)(C)C)C(=O)C(=O)NC1CC1]
74
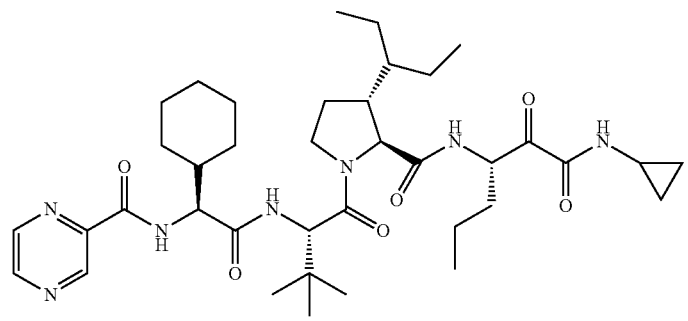 [SMILES: CCC[C@H](NC(=O)[C@@H]1[C@@H](C(CC)CC)CCN1C(=O)[C@@H](NC(=O)[C@@H](NC(=O)c1cnccn1)C1CCCCC1)C(C)(C)C)C(=O)C(=O)NC1CC1]
75
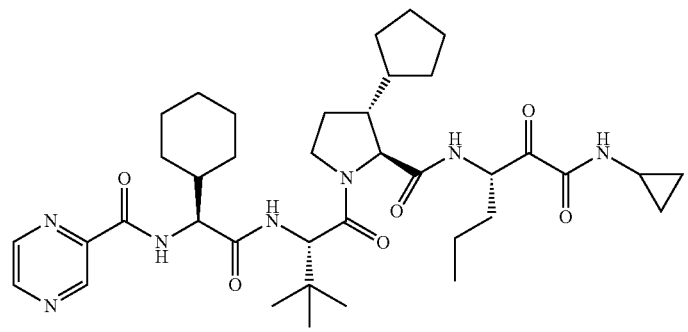 [SMILES: CCC[C@H](NC(=O)[C@@H]1[C@@H](C2CCCC2)CCN1C(=O)[C@@H](NC(=O)[C@@H](NC(=O)c1cnccn1)C1CCCCC1)C(C)(C)C)C(=O)C(=O)NC1CC1]

76

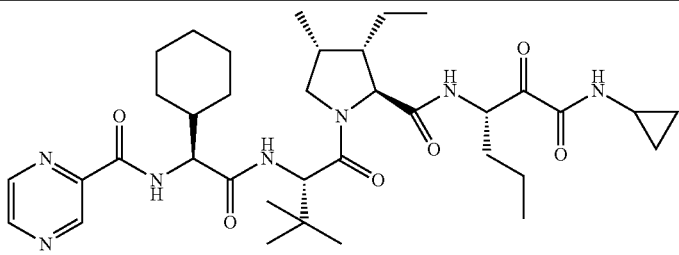

77

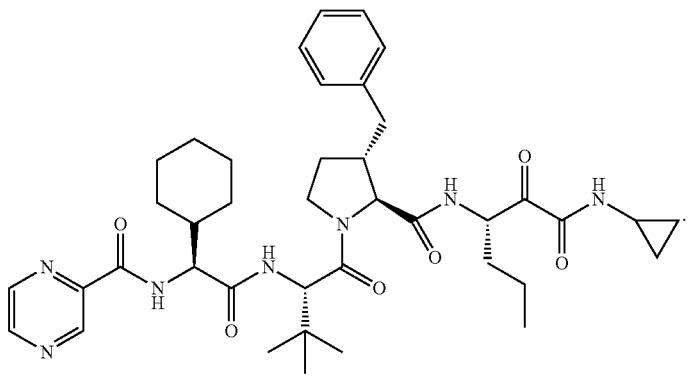 [SMILES: CCC[C@H](NC(=O)[C@@H]1[C@@H](Cc2ccccc2)CCN1C(=O)[C@@H](NC(=O)[C@@H](NC(=O)c1cnccn1)C1CCCCC1)C(C)(C)C)C(=O)C(=O)NC1CC1 ; "."]

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

In another embodiment, the compounds of this invention have the structure and stereochemistry depicted in compounds 1-77.

Any of the embodiments recited above, including those embodiments in the above species, may be combined to produce a preferred embodiment of this invention.

As can be appreciated by the skilled artisan, the synthetic schemes shown are not intended to comprise a comprehensive list of all means by which the compounds described and claimed in this application may be synthesized. Other equivalent schemes, which will be readily apparent to the ordinary skilled organic chemist, may alternatively be used to synthesize various portions of the molecule as illustrated by the general schemes below. Additionally, the various synthetic steps described above may be performed in an alternate sequence or order to give the desired compounds. Other equivalent schemes, which will be readily apparent to the ordinary skilled organic chemist, may alternatively be used to synthesize various portions of the molecule as illustrated by the general schemes below, and the preparative examples that follow.

Abbreviations which are used in the schemes, preparations and the examples that follow are:
DCM: dichloromethane
THF: tetrahydrofuran
DMF: N,N,-dimethylformamide
EtOAc: ethyl acetate
AcOH: acetic acid
NMM: N-methylmorpholine
NMP: N-methylpyyrolidinone
EtOH: ethanol
t-BuOH: tert-butanol
Et$_2$O: diethyl ether
DMSO: dimethyl sulfoxide
DCCA: dichloroacetic acid
DIEA: diisopropylethylamine
MeCN: acetonitrile
TFA: trifluoroacetic acid
DBU: 1,8-diazabicyclo[5.4.0]undec-7-ene
DEAD: diethyl azodicarboxylate
HOBt: 1-hydroxybenzotriazole hydrate
HOAt: 1-hydroxy-7-azabenzotriazole
EDC: 1-(3-dimethylaminopropyl)-3-ethylcarbodiimide hydrochloride
Boc: tert-butyloxycarbonyl
Boc$_2$O: di-tert-butyldicarbonate
Cbz: benzyloxycarbonyl
Cbz-Cl: benzyl chloroformate
Fmoc: 9-fluorenyl methyloxycarbonyl
SEM: silylethoxymethyl
TBAF: tetrabutylammonium fluoride
Chg: cyclohexylglycine
t-BG: tert-butylglycine
mCBPA: 3-chloroperoxybenzoic acid
DAST: (diethylamino)sulfur trifluoride
TEMPO: 2,2,6,6-tetramethyl-1-piperidinyloxy, free radical
PyBOP: tris(pyrrolidino)bromophosphonium hexafluorophosphate
TBTU or HATU: 2-(1H-benzotriazole-1-yl)-1,1,3,3-tetramethyluronium tetrafluoroborate
DMAP: 4-dimethylaminopyridine
AIBN: 2,2'-azobisisobutyronitrile
rt or RT: room temperature
ON: overnight
ND: not determined
MS: mass spectrometry
LC: liquid chromatography
General Synthetic Methodology:

The compounds of this invention may be prepared in general by methods known to those skilled in the art. Schemes 1-6 below illustrate synthetic routes to the compounds of the present invention. Other equivalent schemes, which will be readily apparent to the ordinary skilled organic chemist, may alternatively be used to synthesize various portions of the molecule as illustrated by the general schemes below, and the preparative examples that follow.

Scheme 1.

Scheme 1:

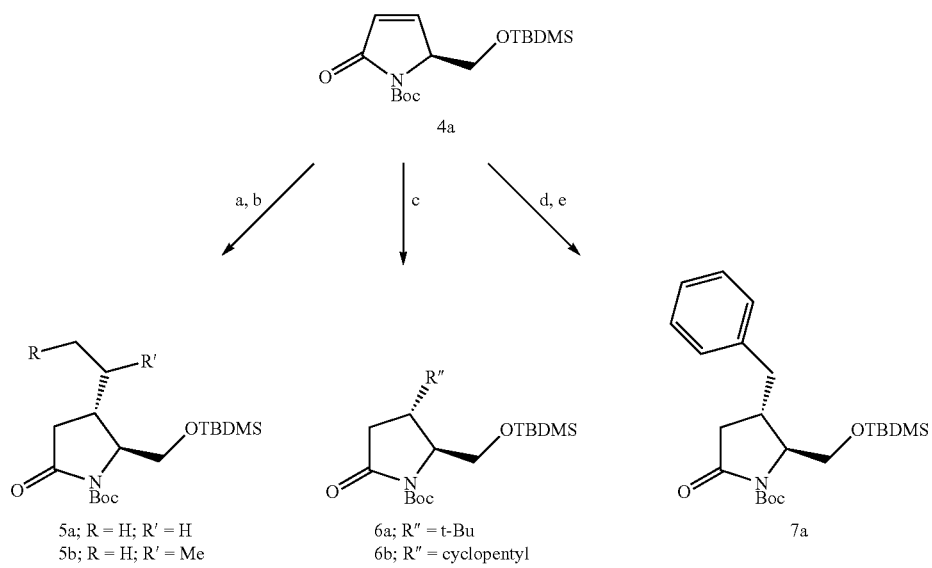

5a; R = H; R' = H
5b; R = H; R' = Me
5c; R = Me; R' = Me

6a; R" = t-Bu
6b; R" = cyclopentyl
6c; R" = 3-pentyl

7a (a) 2-vinyl, 2-propenyl or 2-butenyl-MgBr, CuBr•DMS, ether, -20° C. then TMSCl, -78° C. (65%, 73%, 84%);
(b) 10% Pd—C, H2, 1 atm, EtOH (90%, 92%, 89%) (c) R"ZnBr, THF, -30° C., BF3OEt2 then TMSCl (64%, 40%, 37%);
(d) PhCH(Li)SPh, BuLi, TMEDA, -78° C. (45%); (e) Ra—Ni, acetone/water (1:1), reflux, 12 h (83%).

Scheme 2.

Scheme 2:

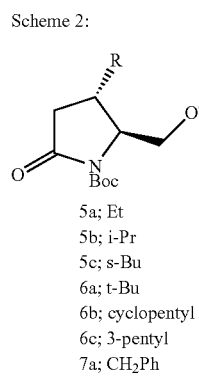

5a; Et
5b; i-Pr
5c; s-Bu
6a; t-Bu
6b; cyclopentyl
6c; 3-pentyl
7a; CH2Ph

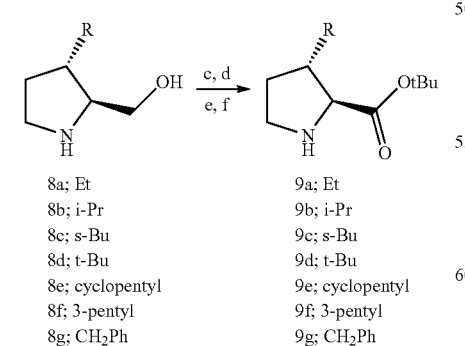

8a; Et
8b; i-Pr
8c; s-Bu
8d; t-Bu
8e; cyclopentyl
8f; 3-pentyl
8g; CH2Ph

9a; Et
9b; i-Pr
9c; s-Bu
9d; t-Bu
9e; cyclopentyl
9f; 3-pentyl
9g; CH2Ph (a) HCl gas, EtOAc, -20° C. (80%-90%); (b) LAH, THF, reflux (85%-90%);
(c) CbzCl, K2CO3, THF:H2O (1:1) (60%-85%); (d) Jones, acetone, (70%-80%);
(e) isobutylene, H2SO4 cat., DCM (67%-85%); (f) 10% Pd—C, H2, 1 atm, EtOAc (90%-95%).

Scheme 3

Scheme 3:

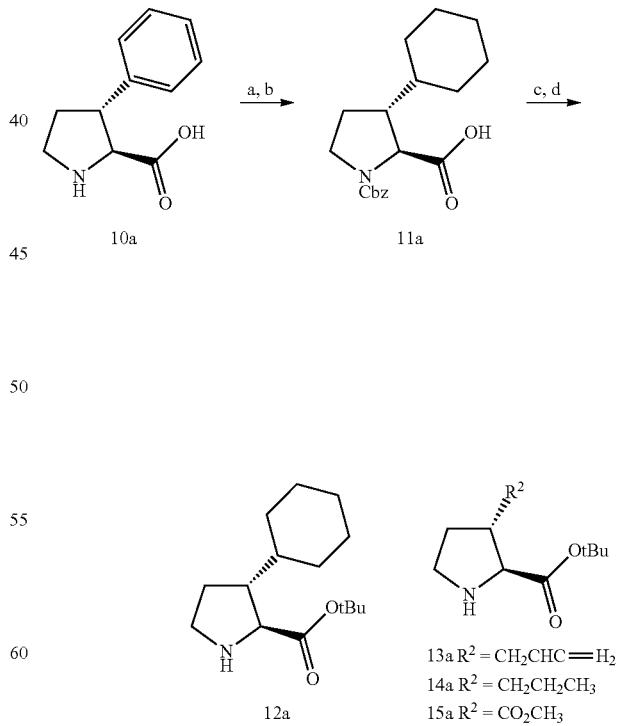

13a R² = CH2CHC═H2
14a R² = CH2CH2CH3
15a R² = CO2CH3

(a) PtO2, EtOH/AcOH/H2O (7/2/1), H2, 50 psi;
(b) CbzCl, Na2CO3, acetone:H2O (1:1) (90%, two steps);
(c) isobutylene, H2SO4 cat., CH2Cl2;
(d) 10% Pd—C, H2, 1 atm, EtOH (84%, two steps).

Scheme 4:

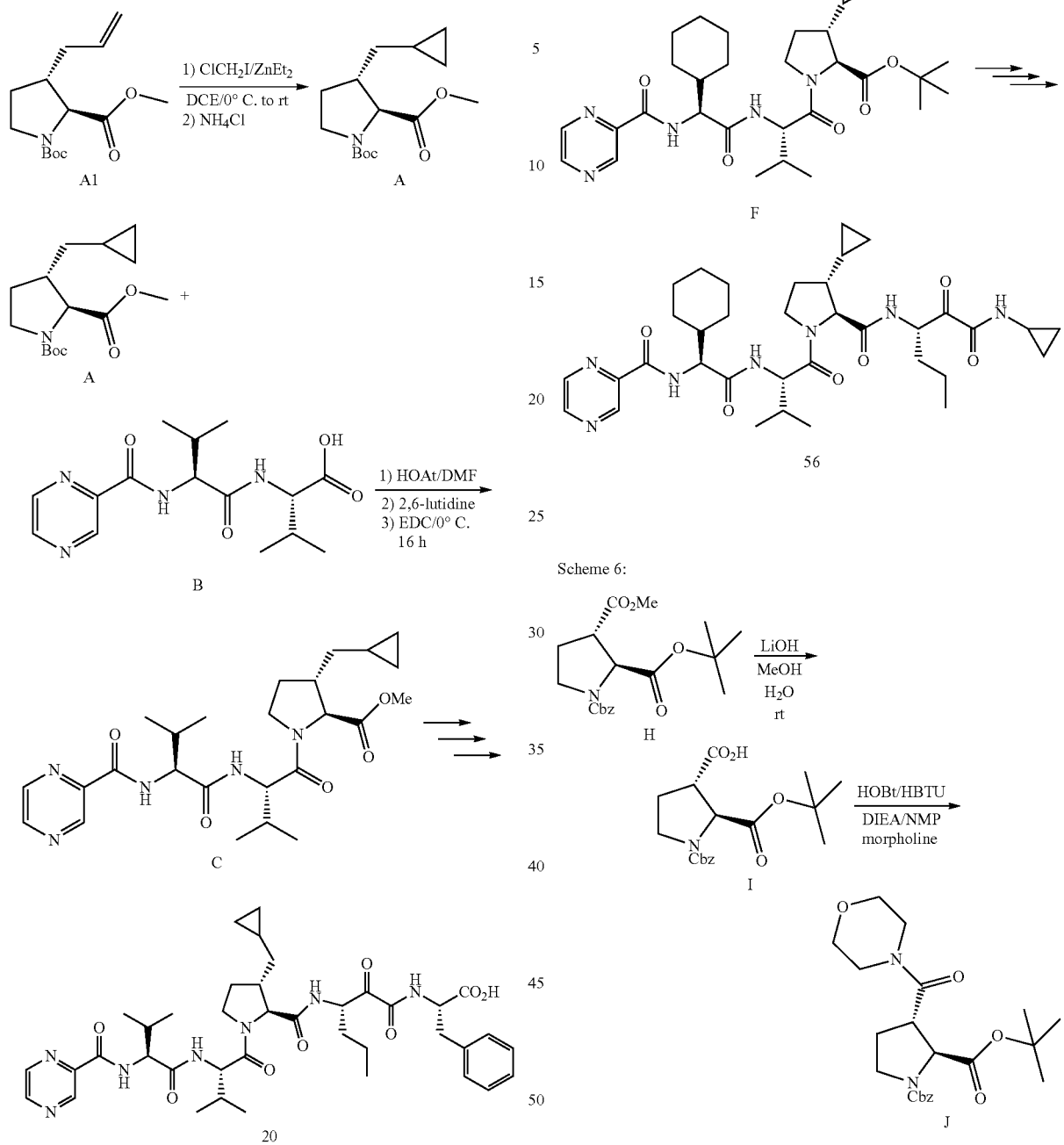

Scheme 5:

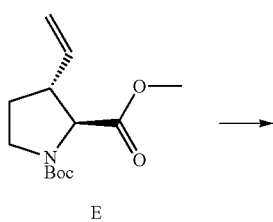

Scheme 1-6 above provide synthetic pathways for the preparation of the compounds of this invention. Many of the starting proline derivatives may be purchased commercially from chemical suppliers known to those in the art. Intermediate A1 may be prepared according to the procedure described in *J. Med. Chem.* 39, p. 2367 (1996).

Although certain embodiments are depicted and described below, it will be appreciated that compounds of this invention can be prepared according to the methods described generally above using appropriate starting materials generally available to one of ordinary skill in the art.

Another embodiment of this invention provides a pharmaceutical composition comprising a compound of formula I or a pharmaceutically acceptable salt thereof. According to another embodiment, the compound of formula I is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to another embodiment, the compositions of this invention are formulated for pharmaceutical administration to a mammal. In another embodiment the compositions of this invention are formulated for pharmaceutical administration to a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In another embodiment, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). In another embodiment, such preparations contain from about 20% to about 80% active compound.

When the compositions of this invention comprise a combination of a compound of formula I and one or more additional therapeutic or prophylactic agents, both the compound and the additional agent should be present at dosage levels of between about 10 to 100% and in another embodiment between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In another embodiment, the pharmaceutical compositions are formulated for oral administration.

In one embodiment, the compositions of this invention additionally comprise another agent, including a cytochrome P-450 inhibitor. Such cytochrome P-450 inhibitors include, but are not limited to, ritonavir.

In another embodiment, the compositions of this invention additionally comprise another anti-viral agent, including an anti-HCV agent. Such anti-viral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including but not limited to, helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. In another embodiment, the methods of this invention are used to treat a patient suffering from a HCV infection. Such treatment may completely eradicate the viral infection or reduce the severity thereof. In another embodiment, the methods of this invention are used to treat a patient suffering from a HCV infection wherein the patient is a human being.

In an alternate embodiment, the methods of this invention additionally comprise the step of administering to said patient an anti-viral agent preferably an anti-HCV agent. Such anti-viral agents include, but are not limited to, immunomodulatory agents, such as $\alpha$-, $\beta$-, and $\gamma$-interferons, pegylated derivatized interferon-$\alpha$ compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention.

Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as shunts, stents, etc.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. In another embodiment, the viral serine protease isolated by this method is HCV NS3-NS4A protease.

In order that this invention be more fully understood, the following preparative and testing examples are set forth. These examples are for the purpose of illustration only and are not to be construed as limiting the scope of the invention in any way.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_t$(min)" refers to the HPLC retention time, in minutes, associated with the compound. The HPLC retention times listed were either obtained from the mass spec. data or using the following method:
Instrument: Hewlett Packard HP-1050;
Column: YMC $C_{18}$ (Cat. No. 326289C46);
Gradient/Gradient Time: 10-90% $CH_3CN/H2O$ over 9 minutes, then 100% $CH_3CN$ for 2 minutes;
Flow Rate: 0.8 ml/min;
Detector Wavelength: 215 nM and 245 nM.

Chemical naming for selected compounds herein was accomplished using the naming program provided by CambridgeSoft Corporations ChemDraw Ultra®, version 7.0.1.

Example 1

Pyrazine-2-carboxylic acid (cyclohexyl-{1-[2-(1-cyclopropylaminooxalyl-butylcarbamoyl)-3-isopropyl-pyrrolidine-1-carbonyl]-2,2-dimethyl-propylcarbamoyl}-methyl)-amide (56)

To a stirring suspension of copper bromide-dimethylsulfide (9.1 g, 44.28 mmol) in 100 mL of dry ether at –20° C. was added isopropenyl magnesium bromide 0.09M (100 mL). After 15 min. of stirring, the temperature was lowered to –78° C. and enone 4a (4.0 g, 8.86 mmol, prepared according to procedure in JACS, 117, p. 10775, (1995)) in 50 mL of ether was added followed by TMSCl (2.25 mL, 18 mmol). The reaction mixture was stirred at –78° C. for 1 h and quenched with 100 mL of ammonium hydroxide-ammonium chloride solution (1:4). Extracted with ether and the organic phase was washed to remove all the copper salts. The ether layer was dried with sodium sulfate and concentrated in vacuo to an oil that was subjected to flash chromatography (ether-hexanes (2:3) to provide 3.5 g (73%) of the desired intermediate olefin.
$^1$H NMR (CDCl$_3$) δ 4.8 (d, 2H); 3.8 (m, 2H); 3.7 (d, 1H); 2.8 (m, 2H); 2.2 (d, 1H); 1.7 (s, 3H); 1.5 (s, 9H); 0.8 (s, 9H); 0.1 (s, 3H); 0.08 (s, 3H) ppm.

Hydrogenation with 10% Pd—C under 1 atmosphere of hydrogen provided 3.5 g (100%) of the desired proline 5b.

HCl gas was bubbled 5 minutes to a solution of 5b (3.5 g, 6.47 mmol) in 50 mL of ethyl acetate at –20° C. Stirred at –20° C. for 30 minutes then warmed up at rt and stirred for 1 h. It was concentrated in vacuo to 1.71 g (100%) of an oil that was reduced with 2.5 equivalent of a 1M LAH in THF solution under reflux for 4 h. Cooled and subjected to a Fieser work up which provided 1.35 g (85%) of the desired compound 8b. 1H NMR (CDCl$_3$) δ 4.0 (dd, 1H); 3.6 (m, 1H); 3.4 (m, 1H); 3.3 (m, 1H); 3.2 (m, 1H); 2.2 (m, 1H); 1.8 (m, 3H); 1.0 (d, 3H); 0.9 (d, 3H) ppm.

To a solution of potassium carbonate (190 mg, 1.38 mmol) in 4 mL of water at rt with stirring, was added 8b (357 mg, 2.5 mmol) in 5 mL of THF. The solution was cooled to –2° C. and Cbz chloride (0.447 mL, 3.13 mmol) was added dropwise maintaining the temperature at 0 to –2° C. It was stirred for an additional 15 minutes, poured into water-ice. The aqueous phase was saturated with salt and the organic phase separated. Further extraction with ethyl acetate was necessary to extract all the compound. The combined organics were washed with HCl 5%, water and brine, dried with sodium sulfate and concentrated in vacuo to 416 mg (60%) on benzoylated hydroxymethylpyrrolidine intermediate. 328 mg of this material was oxidized with Jones reagent to provide 260 mg (75%) of the proline intermediate. The above proline (260 mg, 0.889 mmol) was esterified with isobutylene in dichloromethane with a catalytic amount of concentrated sulfuric acid at rt in a seal vessel for 48 h to provide 289 mg (96%) of the intermediate ester. 1H NMR (CDCl$_3$) δ 7.5 (m, 5H); 5.1 (m, 2H); 4.1 (dd, 1H); 3.6 (m, 1H); 3.5 (m, 1H); 2.1 (m, 2H); 1.7 (m, 2H); 1.5 (s, 9H); 1.1 (d, 3H); 1.0 (d, 3H) ppm.

Hydrogenation with 10% Pd/C in ethyl acetate gave 290 mg (100%) of the desired compound 9b.

To a solution of Cbz-tert-butyl glycine (271 mg, 1.02 mmol) in 2 mL of DCM at 0° C. was added EDC (235 mg, 1.23 mmol), HOBt (203 mg, 1.33 mmol) and DIEA (0.534 mL, 3.07 mmol). The resulting mixture was stirred at 0° C. for 15 min. after which, the above amino ester 9b was slowly added in 2 mL of DCM. The resulting reaction mixture was stirred at rt for 16 h. Concentrated to a residue that was redissolved in EtOAc. Successive washes with 0.5N HCL, satd' aqueous NaHCO$_3$ and brine gave after drying (Na$_2$SO$_4$) and concentration in vacuo the desired product which was subjected to flash chromatography (20% EtOAc/80% hexanes) to provide 480 mg (100%) of pure dipeptide. 1H NMR (CDCl$_3$) δ 4.2 (d, 2H); 4.0 (t, 1H); 3.5 (m, 1H); 2.0 (m, 3H0; 2.8 (m, 2H); 1.5 (s, 9H); 1.1 (s, 9H); 1.0 (d, 3H); 0.9 (d, 3H) ppm.

The Cbz group of the dipeptide was removed as described above and the resulting aminoester dipeptide was coupled to Cbz-cyclohexyl glycine shown in the next step.

To a solution of Cbz-cyclohexyl glycine (289 mg, 1 mmol) in 2 mL of DCM at 0° C. was added EDC (228 mg, 1.19 mmol), HOBt (190 mg, 1.29 mmol) and DIEA (0.517 mL, 2.97 mmol). The resulting mixture was stirred at 0° C. for 15 min. after which, the above amino ester was slowly added in 2 mL of DCM. The resulting reaction mixture was stirred at rt for 16 h. Concentrated to a residue that was redissolved in EtOAc. Successive washes with 0.5N HCL, satd' aqueous NaHCO$_3$ and brine gave after drying (Na$_2$SO$_4$) and concentration in vacuo the desired product which was subjected to flash chromatography (20% EtOAc/80% hexanes) to provide 556 mg (90%) of pure tripeptide. The Cbz group of the tripeptide was removed as described above and the resulting aminoester tripeptide was coupled to 1,4-pyrazine carboxylic acid shown in the next step.

To a solution of 1,4-pyrazine carboxylic acid (110 mg, 0.891 mmol)) in 2 mL of DCM was added PyBrOP (457 mg, 0.98 mmol and DIEA (0.465 mL, 2.67 mmol). The resulting mixture was stirred at rt for 15 min. after which, the above amino ester was slowly added in 2 mL of DCM. The resulting reaction mixture was stirred at rt for 16 h. Concentrated to a residue that was redissolved in EtOAc. Successive washes with 0.5N HCL, sat'd aqueous NaHCO$_3$ and brine gave after drying (Na$_2$SO$_4$) and concentration in vacuo the desired product which was subjected to flash chromatography (50% EtOAc/50% hexanes) to provide 410 mg (79%) of pure capped tripeptide with consistent $^1$H NMR (CDCl$_3$).

The t-butyl ester group of the capped tripeptide (410 mg, 0.688 mmol) was cleaved with a 1:1 mixture of TFA-DCM at rt for 45 minutes and concentrated in vacuo. The resulting aminoester tripeptide was coupled to hydroxyamide detailed in the next step.

To a stirring solution of the capped tripeptide acid from above in 6 mL of dry DMF at 0° C. was added, PyBOP (376 mg, 0.722 mmol) followed by NMM (0.226 mL, 2.06 mmol). The reaction mixture was stirred for 1 h at rt after which a solution of hydroxyamide (168 mg, 0.758 mmol) and 0.226 mL of NMM was slowly added. The coupling reaction was stirred for 16 h, diluted with ethyl acetate and was successively washed with; water (3×), citric acid 10%, water and brine. The organic layer was dried (Na$_2$SO$_4$) and concentrated in vacuo. Flash chromatography (2.5% MeOH/97.5% ethyl acetate) provided 362 mg of hydroxy amide tetrapeptide that was oxidized with Dess-Martin periodinane reagent (650 mg, 1.53 mmol) and t-butanol (0.65 mL) in 5 mL of DCM at rt for 3 h. The reaction mixture was quenched with sodium thiosulfate 1M solution (2 mL) and stirred until the two phases are clearly separated. The organic layer was diluted with 5 more mL of DCM and washed (3×) with 10% potassium carbonate aqueous solution (5 mL), dried (Na$_2$SO$_4$) and concentrated in vacuo. Flash chromatography (2.5% MeOH/ 97.5% ethyl acetate) provided 270 mg of ketoamide tetrapeptide 56. LCMS M+H=706.42, M−H=704.42. Retention Time (10-90% MeCN—H$_2$O with 0.1% TFA over 9 minutes)=7.73-8.81 min. LCMS M+H=682.2.

Example 2

3-tert-Butyl-2-(tert-butyl-dimethyl-silanyloxymethyl)-5-oxo-pyrrolidine-1-carboxylic acid tert-butyl ester (6a)

t-Butyl zinc bromide 0.5M solution in THF (3.7 mL, 1.83 mmol) was added to a solution of enone 4a (280 mg, 0.85 mmol) in THF containing BF$_3$OEt$_2$ (350 uL, 2.75 mmol) and TMSCl (465 uL) at −30° C. over a period of 5 minutes. The heterogeneous mixture was stirred at −30° C. for 3.5 h than quenched with sat'd NH$_4$Cl solution. Extracted with ether (3×) and the combined extract were washed with brine, dried with sodium sulfate and concentrated in vacuo. Flash chromatography (10% ethyl acetate-hexanes) provided 210 mg (64%) of 6a. $^1$H NMR (CDCl$_3$) δ 3.9 (s, 1H); 3.8 (dd, 1H); 3.5 (d, 1H); 2.8 (dd, 1H); 2.3 (d, 1H); 1.9 (d, 1H); 1.4 (s, 9H); 0.9 (s, 18H); 0.1 (s, 3H); 0.05 (s, 3H) ppm.

Example 3

3-Benzyl-2-(tert-butyl-dimethyl-silanyloxymethyl)-5-oxo-pyrrolidine-1-carboxylic acid tert-butyl ester (7a)

To a mixture of n-butyllithium (5.5 mL, 0.0086 mol) and THF at −78° C., was added TMEDA and benzylphenylsulfide (1.91 g, 0.0095 mol). The colorless solution turned pale yellow. After 15 min of stirring at −78° C., the pyrolidone 4 (2.4 g, 0.0073 mol) in 10 mL of THF was added dropwise. After the addition was completed, the reaction mixture was stirred for 1 h at −78° C. The reaction was quenched with satd' NH$_4$Cl solution and the mixture warmed to rt and poured into water. Ether mixture was extracted with ethyl ether and the organic phase was washed with brine, dried and concentrated in vacuo. Flash chromatography (20% ethyl acetate-hexane) provided 1.69 g (45%) of the desired intermediate. Reduction with 16.9 g of Ra—Ni in refluxing acetone-water (1:1) for 12 h provided, after chromatography (2% acetone-chloroform), 1.11 g (83%) of the desired compound 7. $^1$H NMR (CDCl$_3$) δ 7.3 (m, 5H); 3.8 (m, 2H); 3.7 (d, 1H); 2.7-2.9 (m, 3H); 2.1 (m, 2H); 1.5 (s, 9H); 1.7 (s, 9H); 0.1 (s, 6H) ppm.

Example 4

Pyrazine-2-carboxylic acid ({1-[3-benzyl-2-(1-cyclopropylaminooxalyl-butylcarbamoyl)-pyrrolidine-1-carbonyl]-2,2-dimethyl-propylcarbamoyl}-cyclohexyl-methyl)-amide (65)

Prepared as described above in scheme 1 starting with intermediate 7a to give 65 with consistent analytical data. Retention Time (10-90% MeCN—H$_2$O with 0.1% TFA over 6 minutes)=8.0-9.2 min. LCMS M+H=730.2

Example 5

3-Cyclohexyl-pyrrolidine-2-carboxylic acid tert-butyl ester (12a)

3-Phenyl proline 10a was hydrogenated with catalytic platinum oxide in ethanol/acetic acid/water (7/2/1) under 50 psi of hydrogen for 18 h to give 3-cyclohehyl proline quantitatively. Compound 12a was prepared according to benzoylation and esterification from example 1; step 3.

Example 6

3-Cyclopropylmethyl-pyrrolidine-1,2-dicarboxylic acid 1-tert-butyl ester 2-methyl ester (A)

In a round bottom flask, a solution of the allyl proline (358 mg, 1.33 mmol) in dry DCE was cooled to 0° C., and diethyl zinc in hexanes 15% (5.5 mL, 6.63 mmol) was added slowly via a syringe. To this solution was added chloroiodomethane (967 uL, 13.3 mmol) dropwise. The solution was stirred at 0° C. for 20 minutes, allowed to warm to rt an stirred for 1 h. The reaction mixture was cooled to 0° C. and quenched with satd' NH$_4$Cl solution and stirred vigourously for 10 minutes. Extracted with dichloromethane, dried with sodium sulfate and concentrated in vacuo. Chromatography (20% ethyl acetate-hexanes) gave 65 mg (17%) of the desired product A.

¹H NMR (CDCl₃) δ 3.8 (s, 1H); 3.7 (s, 3H); 3.6-3.4 (m, 2H); 2.4 (m, 1H); 2.3 (m, 1H); 1.3 (m, 3H); 0.8 (m, 1H); 0.5 (m, 2H); 0.2 (m, 2H) ppm.

Example 7

3-Cyclopropylmethyl-1-(3-methyl-2-{3-methyl-2-[(pyrazine-2-carbonyl)-amino]-butyrylamino}-butyryl)-pyrrolidine-2-carboxylic acid methyl ester (C)

Tripeptide C was prepared by the coupling of cyclopropylmethyl proline A (41 mg, 0.16 mmol) and capped dipeptide B (52 mg, 0.16 mmol) with EDC/HOAt to give 60 mg (77%) of the desired tripeptide C after chromatography (1:1 ethyl acetate-hexanes). ¹H NMR (CDCl₃) δ 9.4 (s, 1H); 8.8 (s, 1H); 8.5 (s, 1H); 8.2 (d, 1H); 6.5 (d, 1H); 4.6 (t, 1H); 4.5 (t, 1H); 4.2 (m, 1H); 3.8 (s, 3H); 3.7 (m, 2H); 2.3 (m, 4H); 2.2 (m, 2H); 1.5 (s, 12H); 1.3 (m, 2H); 1.0 (m, 2H); 0.5 (m, 2H) ppm.

Example 8

2-(3-{[3-Cyclopropylmethyl-1-(3-methyl-2-{3-methyl-2-[(pyrazine-2-carbonyl)-amino]-butyrylamino}-butyryl)-pyrrolidine-2-carbonyl]-amino}-2-oxo-hexanoylamino)-3-phenyl-propionic acid (D)

Prepared as in example 1. Retention Time (10-90% MeCN—H₂O with 0.1% TFA over 6 minutes)=7.55-7.78 min. LCMS M+H=748.3.

Example 9

HCV Replicon Cell Assay Protocol

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then media A was diluted into a final concentration of 100,000 cells per ml with. 10,000 cells in 100 ul were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A Taqman real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The $IC_{50}$ (concentration at which 50% inhibition of HCV RNA level is observed) was calculated from the titration curve of any given compound.

Example 10

HCV Ki Assay Protocol

HPLC Microbore Method for Separation of 5AB Substrate and Products
Substrate: NH₂-Glu-Asp-Val-Val-(alpha)Abu-Cys-Ser-Met-Ser-Tyr-COOH
A stock solution of 20 mM 5AB (or concentration of your choice) was made in DMSO w/0.2M DTT. This was stored in aliquots at −20 C.
Buffer: 50 mM HEPES, pH 7.8; 20% glycerol; 100 mM NaCl
Total assay volume was 100 μL

|  | X1 (μL) | conc. in assay |
|---|---|---|
| Buffer | 86.5 | see above |
| 5 mM KK4A | 0.5 | 25 μM |
| 1M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30 C for ~5-10 min.

2.5 μL of appropriate concentration of test compound was dissolved in DMSO (DMSO only for control) and added to each well. This was incubated at room temperature for 15 min.

Initiated reaction by addition of 20 μL of 250 μM 5AB substrate (25 μM concentration is equivalent or slightly lower than the Km for 5AB).

Incubated for 20 min at 30 C.
Terminated reaction by addition of 25 μL of 10% TFA
Transferred 120 μL aliquots to HPLC vials
Separated SMSY product from substrate and KK4A by the following method:
Microbore Separation Method:
Instrumentation: Agilent 1100
Degasser G1322A
Binary pump G1312A
Autosampler G1313A
Column thermostated chamber G1316A
Diode array detector G1315A Column:
Phenomenex Jupiter; 5 micron C18; 300 angstroms; 150×2 mm; P/O 00E-4053-B0
Column thermostat: 40 C
Injection volume: 100 μL
Solvent A=HPLC grade water+0.1% TFA
Solvent B=HPLC grade acetonitrile+0.1% TFA

| Time (min) | % B | Flow (ml/min) | Max press. |
| --- | --- | --- | --- |
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

Table 1 below depicts $IC_{50}$ data for certain compounds of the invention.
Compounds with Ki's ranging from 0.5 μM to >1 μM are designated A. Compounds with Ki's ranging from 0.5 μM to 0.1 μM are designated B. Compounds with Ki's below 0.1 μM are designated C. Compounds with $IC_{50}$'s ranging from 1 μM to >10 μM are designated A. Compounds with $IC_{50}$'s ranging from 1 μM to 0.5 μM are designated B. Compounds with $IC_{50}$'s below 0.5 μM are designated C. ND means no data.

TABLE 1

| Compound | Ki | $IC_{50}$ |
| --- | --- | --- |
| 5 | C | ND |
| 15 | B | ND |
| 16 | B | ND |
| 19 | B | ND |
| 20 | B | ND |
| 22 | B | ND |
| 25 | B | ND |
| 26 | C | ND |
| 27 | C | ND |
| 28 | C | ND |
| 29 | C | ND |
| 30 | B | ND |
| 31 | C | ND |
| 32 | B | ND |
| 33 | B | ND |
| 35 | A | ND |
| 36 | B | ND |
| 39 | C | B |
| 41 | A | C |
| 42 | C | ND |
| 43 | B | ND |
| 44 | B | B |
| 45 | A | ND |
| 46 | B | ND |
| 50 | B | ND |
| 51 | B | ND |
| 52 | C | C |
| 53 | B | ND |
| 54 | B | A |
| 55 | C | B |
| 56 | B | ND |
| 57 | C | ND |
| 60 | ND | A |
| 62 | C | B |
| 63 | C | B |
| 64 | B | A |
| 65 | C | B |
| 66 | B | B |
| 67 | A | A |
| 68 | C | C |
| 69 | C | C |

TABLE 1-continued

| Compound | Ki | $IC_{50}$ |
| --- | --- | --- |
| 71 | C | A |
| 72 | C | B |
| 73 | B | A |
| 74 | B | A |
| 75 | B | A |
| 76 | B | A |
| 77 | B | A |

We claim:
1. A compound according to the formula:

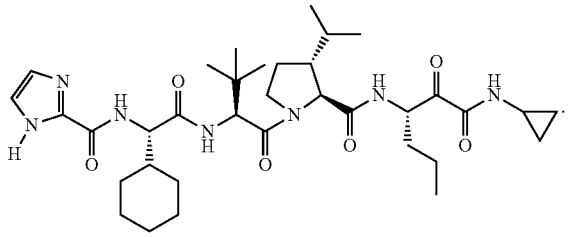

2. A pharmaceutical composition comprising a compound according to claim 1 or a pharmaceutically acceptable salt or mixtures thereof in an amount effective to inhibit a serine protease; and a acceptable carrier, adjuvant or vehicle.

3. The composition according to claim 2, wherein said composition is formulated for administration to a patient.

4. The composition according to claim 3, wherein said composition comprises an additional agent selected from an immunomodulatory agent; an antiviral agent; a second inhibitor of HCV protease; an inhibitor of another target in the HCV life cycle; and a cytochrome P-450 inhibitor; or combinations thereof.

5. The composition according to claim 2, wherein said immunomodulatory agent is α-, β-, or γ-interferon or thymosin; said antiviral agent is ribavirin, amantadine, or telbivudine; or said inhibitor of another target in the HCV life cycle is an inhibitor of HCV helicase, polymerase, or metalloprotease.

6. The composition according to claim 4, wherein said cytochrome P-450 inhibitor is ritonavir.

7. The method according to claim 1, wherein said serine protease is an HCV NS3 protease.

8. A method of treating an HCV infection in a patient comprising the step of administering to said patient a composition according to claim 3.

9. The method according to claim 8, comprising the additional step of administering to said patient an additional agent selected from an immunomodulatory agent; an antiviral agent; a second inhibitor of HCV protease; an inhibitor of another target in the HCV life cycle; or combinations thereof; wherein said additional agent is administered to said patient as part of said composition according to claim 3 or as a separate dosage form.

10. The method according to claim 9, wherein said immunomodulatory agent is α-, β-, or γ-interferon or thymosin; said antiviral agent is ribavarin or amantadine; or said inhibitor of another target in the HCV life cycle is an inhibitor of HCV helicase, polymerase, or metalloprotease.

11. A method of eliminating or reducing HCV contamination of a biological sample or medical or laboratory equipment, comprising the step of contacting said biological sample or medical or laboratory equipment with a composition according to claim 2.

12. The method according to claim 11, wherein said sample or equipment is selected from blood, other body fluids, biological tissue, a surgical instrument, a surgical garment, a laboratory instrument, a laboratory garment, a blood or other body fluid collection apparatus; a blood or other body fluid storage material.

13. The method according to claim 12, wherein said body fluid is blood.

* * * * *